US007347879B2

(12) United States Patent
Sabelle et al.

(10) Patent No.: US 7,347,879 B2
(45) Date of Patent: Mar. 25, 2008

(54) SULFUR-CONTAINING SECONDARY PARA-PHENYLENEDIAMINES DYE COMPOSITIONS COMPRISING SUCH PARA-PHENYLENEDIAMINES, PROCESSES, AND USES THEREOF

(75) Inventors: Stéphane Sabelle, Paris (FR); Eric Metais, St-leu-le-Foret (FR)

(73) Assignee: L'Oreál, S.A., Paris (FR)

( * ) Notice: Subject to any disclaimer, the term of this patent is extended or adjusted under 35 U.S.C. 154(b) by 180 days.

(21) Appl. No.: 11/066,457

(22) Filed: Feb. 28, 2005

(65) Prior Publication Data

US 2006/0005321 A1 Jan. 12, 2006

Related U.S. Application Data

(60) Provisional application No. 60/570,896, filed on May 14, 2004.

(30) Foreign Application Priority Data

Feb. 27, 2004 (FR) .................................. 04 02016

(51) Int. Cl.
*A61K 7/13* (2006.01)
(52) U.S. Cl. ..................... 8/405; 8/406; 8/408; 8/409; 8/410; 8/415; 8/421; 8/549; 8/575; 564/440
(58) Field of Classification Search ............. 8/405, 8/406, 408, 409, 410, 415, 421, 549, 575; 564/440

See application file for complete search history.

(56) References Cited

U.S. PATENT DOCUMENTS

| 2,241,769 | A | | 5/1941 | Dickey et al. | |
|---|---|---|---|---|---|
| 3,561,912 | A | | 2/1971 | Boosen et al. | |
| RE30,199 | E | | 1/1980 | Rose et al. | |
| 4,425,132 | A | * | 1/1984 | Grollier et al. ................. | 8/405 |
| 4,823,985 | A | | 4/1989 | Grollier et al. | |
| 4,979,961 | A | | 12/1990 | Junino et al. | |
| 5,032,137 | A | * | 7/1991 | Junino et al. ................. | 8/410 |
| 5,061,289 | A | | 10/1991 | Clausen et al. | |
| 5,380,340 | A | | 1/1995 | Neunhoeffer et al. | |
| 5,534,267 | A | | 7/1996 | Neunhoeffer et al. | |
| 5,663,366 | A | | 9/1997 | Neunhoeffer et al. | |
| 5,708,151 | A | | 1/1998 | Mockli | |
| 5,744,622 | A | | 4/1998 | Russ et al. | |
| 5,766,576 | A | | 6/1998 | Lowe et al. | |
| 6,099,592 | A | | 8/2000 | Vidal et al. | |
| 6,284,003 | B1 | | 9/2001 | Rose et al. | |
| 6,730,789 | B1 | | 5/2004 | Birault et al. | |

FOREIGN PATENT DOCUMENTS

| DE | 635 298 | 9/1936 |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 326 863 A2 | 8/1989 |
| EP | 0 714 954 B1 | 6/1996 |
| EP | 0 717 084 A1 | 6/1996 |
| EP | 0 770 375 B1 | 5/1997 |
| FR | 1 505 471 | 12/1967 |
| FR | 2 586 913 A1 | 3/1987 |
| FR | 2 630 438 A1 | 10/1989 |
| FR | 2 733 749 A1 | 11/1996 |
| FR | 2 801 308 A1 | 5/2001 |
| GB | 1000404 | 8/1965 |
| GB | 1026978 | 4/1966 |
| GB | 1153196 | 5/1969 |
| JP | 02-019576 A | 1/1990 |
| JP | 05-63124 | 6/1993 |
| JP | 2526099 B2 | 5/1996 |
| WO | WO 94/08969 A1 | 4/1994 |
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 96/18898 A1 | 6/1996 |

OTHER PUBLICATIONS

STIC Search Report dated Mar. 14, 2007.*
Database CHEMABS 'Online!, Chemical Abstracts Service, Columbus, Ohio, US Database accession No. 1957: 51814, Reppe et al., "Vinylation. II. Sulfur-containing vinyl compounds," *Ann.*, 601: 111-128 (1956).
Database CHEMABS 'Online!, Chemical Abstracts Service, Columbus, Ohio, US Database accession No. 1963: 53203, Schimmelschmidt et al., "Preparation and Reactions of 2-aminoethylthiosulfuric acid," *Chemische Berichte*, 96: 38-47 (1963).
Database CHEMABS 'Online!, Chemical Abstracts Service, Columbus, Ohio, US Database accession No. 1995: 955864, Zeid et al., "Reactions with sultones. Synthesis of butane-1,4-sultone derivatives," *Journal de la Societe Algerienne de Chimie*, 4(2): 171-177 (1994).
Database CHEMABS 'Online!, Chemical Abstracts Service, Columbus, Ohio, US Database accession No. 1999: 480553, Udupi et al. "Synthesis and biological activity of some quinazolinone derivatives," *Indian Journal of Heterocyclic Chemistry*, 8(4): 301-304 (1999).
English language Derwent abstract of EP 0 770 375 B1, May 2, 1997.

(Continued)

*Primary Examiner*—Eisa Elhilo
(74) *Attorney, Agent, or Firm*—Finnegan, Henderson, Farabow, Garrett & Dunner, LLP

(57) ABSTRACT

The present disclosure relates to a novel family of sulfur-containing secondary para-phenylenediamines, to processes for preparing them, to compositions for dyeing keratin fibers, for example keratin fibers such as the hair, comprising, in a suitable dyeing medium, at least such one sulfur-containing secondary para-phenylenediamine. The present disclosure also relates to processes for dyeing keratin fibers with the compositions according to the present disclosure and to multi-compartment dyeing kits containing such compositions.

29 Claims, No Drawings

OTHER PUBLICATIONS

English language JPO abstract of Japanese Published Application No. JP 02-019576 A, Jan. 23, 1990, which corresponds to Japanese Patent No. 2526099 B2.

English language Derwent abstract of JP 05-163124, Jun. 23, 1993.

French Search Report for FR 04 02016 (French priority application for U.S. Appl. No. 11/066,457, the present application), Oct. 4, 2004.

Kotsuki et al., "High Pressure Organic Chemistry; XII. A Convenient Synthesis of Aromatic Amines From Activated Aromatic Fluorides," *Synthesis*, 12: 1147-1148 (1990).

Massa et al., "Spiro-[4*H*-Pyrrolo[1,2-a][1,4]Benzodiazepine-4,4'-Piperidine] Derivatives As Potential Nootropic Agents: A Simple One-Pot Synthesis," *Synthetic Communications*, 20(22): 3537-3545 (1990).

* cited by examiner

SULFUR-CONTAINING SECONDARY PARA-PHENYLENEDIAMINES DYE COMPOSITIONS COMPRISING SUCH PARA-PHENYLENEDIAMINES, PROCESSES, AND USES THEREOF

This application claims benefit of U.S. Provisional Application No. 60/570,896, filed May 14, 2004, and French Application No. 04/02016, filed Feb. 27, 2004, which are herein incorporated by reference.

The present disclosure relates to a novel family of sulfur-containing secondary para-phenylenediamines, to their preparation, to cosmetic compositions comprising them, and to processes of dyeing keratin fibers, such as hair, using these compositions.

It is known practice to dye keratin fibers, for instance keratin fibers such as hair, with dye compositions comprising oxidation dye precursors, such as ortho- or para-phenylenediamines, ortho- or para-aminophenols, and heterocyclic compounds, which are generally referred to as oxidation bases. Oxidation bases are colorless or weakly colored compounds which, when combined with oxidizing products, may give rise to colored compounds by a process of oxidative condensation.

It is also known that the shades obtained with oxidation bases may be varied by combining them with couplers or coloration modifiers. The coloration modifiers can be chosen, for example, from aromatic meta-diaminobenzenes, meta-aminophenols, meta-diphenols, and certain heterocyclic compounds such as indole compounds.

The variety of molecules used as oxidation bases and couplers makes it possible to obtain a wide range of colors.

The "permanent" coloration obtained using oxidation dyes should moreover satisfy a certain number of requirements. For example, it should have no toxicological drawbacks, should allow shades of the desired intensity to be obtained, and/or should have good resistance to external agents such as light, bad weather, washing, permanent waving, perspiration, and rubbing.

The dyes should also allow white keratin fibers to be covered, and ideally, should also be as unselective as possible, i.e., allow the smallest possible differences in coloration to be produced over the entire length of the same keratin fiber, which is generally differently sensitized (i.e. damaged) between its end and its root.

The present inventor has just discovered, surprisingly and unexpectedly, a novel family of sulfur-containing secondary para-phenylenediamines capable of giving strong, aesthetic, and sparingly selective colorations in varied shades, and capable of showing good resistance to the various attacking factors to which keratin fibers may be subjected. Accordingly, the present disclosure relates to processes for preparing these sulfur-containing secondary para-phenylenediamines and to their use in the oxidation dyeing of keratin fibers, such as hair.

Another aspect of the present disclosure relates to novel compositions for dyeing keratin fibers, for example human keratin fibers such as hair, comprising at least one sulfur-containing secondary para-phenylenediamine.

The compositions of the present disclosure make it possible to obtain a very strong and sparingly selective coloration of keratin fibers, which is fast, for example light-fast, while at the same time avoiding the degradation of these fibers. In addition, these compositions can have a good toxicological profile.

Still another aspect of the present disclosure relates to dyeing processes using the compositions described herein to dye keratin fibers, for example human keratin fibers such as hair, comprising applying these compositions to keratin fibers. Another aspect of the present disclosure relates to multi-compartment devices or dyeing kits comprising the compositions described herein.

Other characteristics, aspects, and benefits of the present disclosure will emerge even more clearly upon reading the description and the non-limiting examples that follow.

In the context of the present disclosure, the term "alkyl" means a linear or branched $C_1$-$C_{15}$ radical, for example methyl, ethyl, n-propyl, isopropyl, butyl, etc. The term "alkoxy radical," as used herein, means an O-alkyl radical, the alkyl radical having the definition given above, for example methyloxy or ethyloxy. The term "halogen," as used herein, means Cl, Br, I, or F. For the purposes of the present disclosure, the term "aryl" means an unsubstituted aryl radical.

The novel sulfur-containing secondary para-phenylenediamines according to the present disclosure are chosen from compounds of formula (I) and the addition salts thereof:

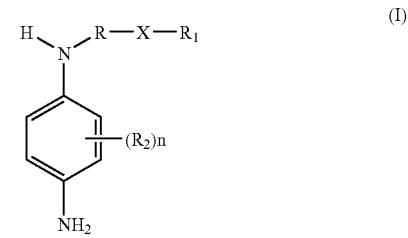

wherein:
X is chosen from $SO_2$ and sulfur;
if X is an $SO_2$ radical, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl radicals; and n is an integer ranging from 1 to 4;

with the exception of the following compounds:

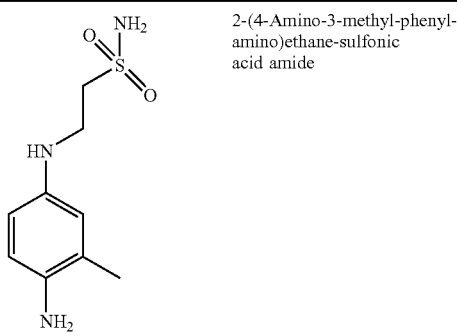
2-(4-Amino-3-methyl-phenylamino)ethane-sulfonic acid amide

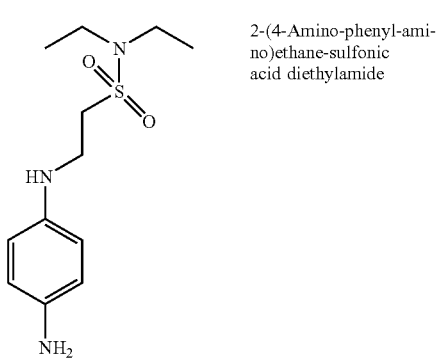
2-(4-Amino-phenyl-amino)ethane-sulfonic acid diethylamide

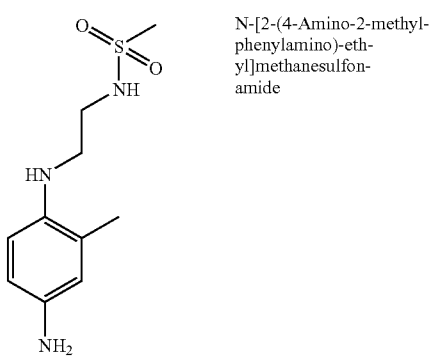
N-[2-(4-Amino-2-methyl-phenylamino)-ethyl]methanesulfonamide

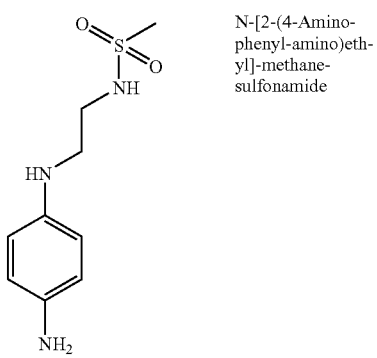
N-[2-(4-Amino-phenyl-amino)ethyl]-methanesulfonamide

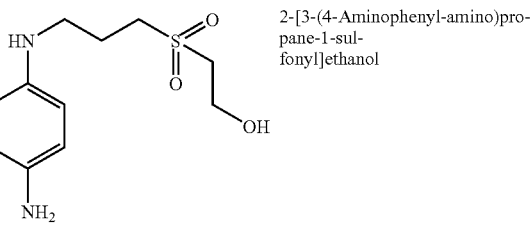
2-[3-(4-Aminophenyl-amino)propane-1-sulfonyl]ethanol

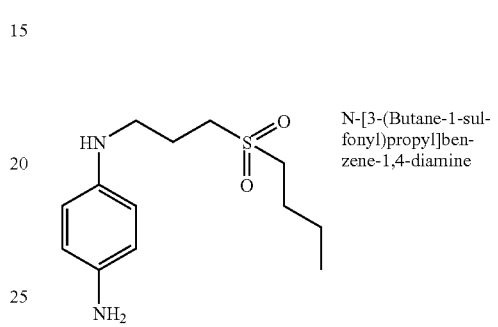
N-[3-(Butane-1-sulfonyl)propyl]benzene-1,4-diamine

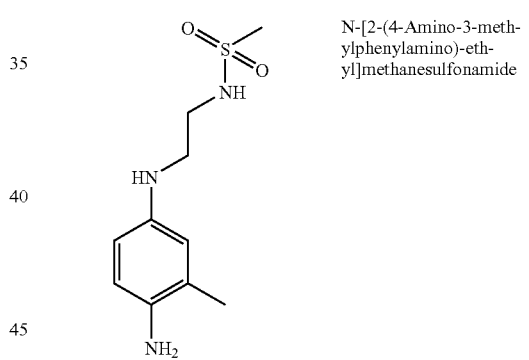
N-[2-(4-Amino-3-methylphenylamino)-ethyl]methanesulfonamide

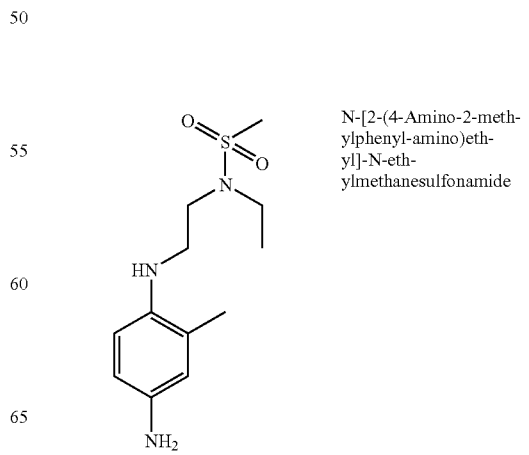
N-[2-(4-Amino-2-methylphenyl-amino)ethyl]-N-ethylmethanesulfonamide

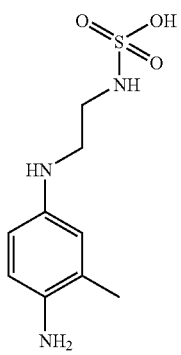

[2-(4-Amino-3-methyl-phenyl-amino)ethyl]-sulfamic acid

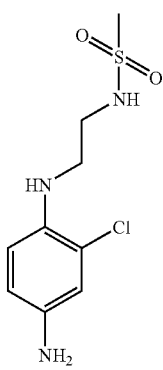

N-[2-(4-Amino-2-chloro-phenylamino)-ethyl]methane-sulfonamide

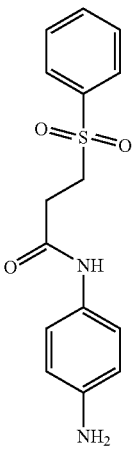

N-[3-(4-Amino-phenyl-amino)propyl-3-oxo]-benzene-sulfonamide

In one embodiment, R is chosen from linear and branched $C_2$-$C_5$ alkylene radicals, which may be substituted with a radical chosen from —OH, —COOCH$_3$, and —COOCH$_2$CH$_3$, wherein at least one carbon atom of the alkylene radical is optionally replaced with at least one heteroatom chosen from oxygen, nitrogen, and sulfur.

In another embodiment, $R_1$ is chosen from alkyl, aryl, arylalkyl, and hydroxyalkyl groups, and secondary and tertiary amine groups.

In another embodiment, $R_2$ is chosen from hydrogen and methyl.

In one embodiment, the sulfur-containing secondary paraphenylenediamines according to the present disclosure are chosen from:

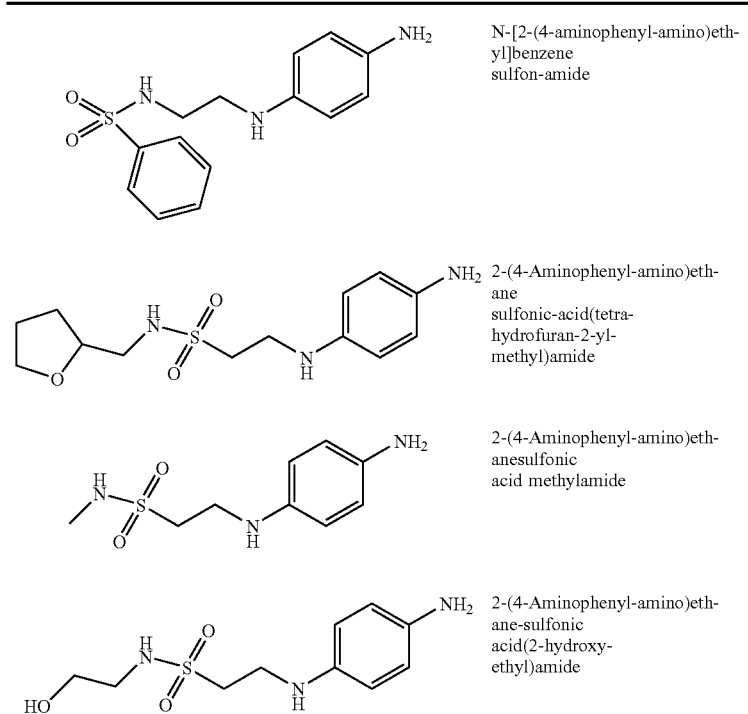

N-[2-(4-aminophenyl-amino)ethyl]benzene sulfon-amide 2-(4-Aminophenyl-amino)ethane sulfonic-acid(tetra-hydrofuran-2-yl-methyl)amide 2-(4-Aminophenyl-amino)ethanesulfonic acid methylamide 2-(4-Aminophenyl-amino)ethane-sulfonic acid(2-hydroxy-ethyl)amide

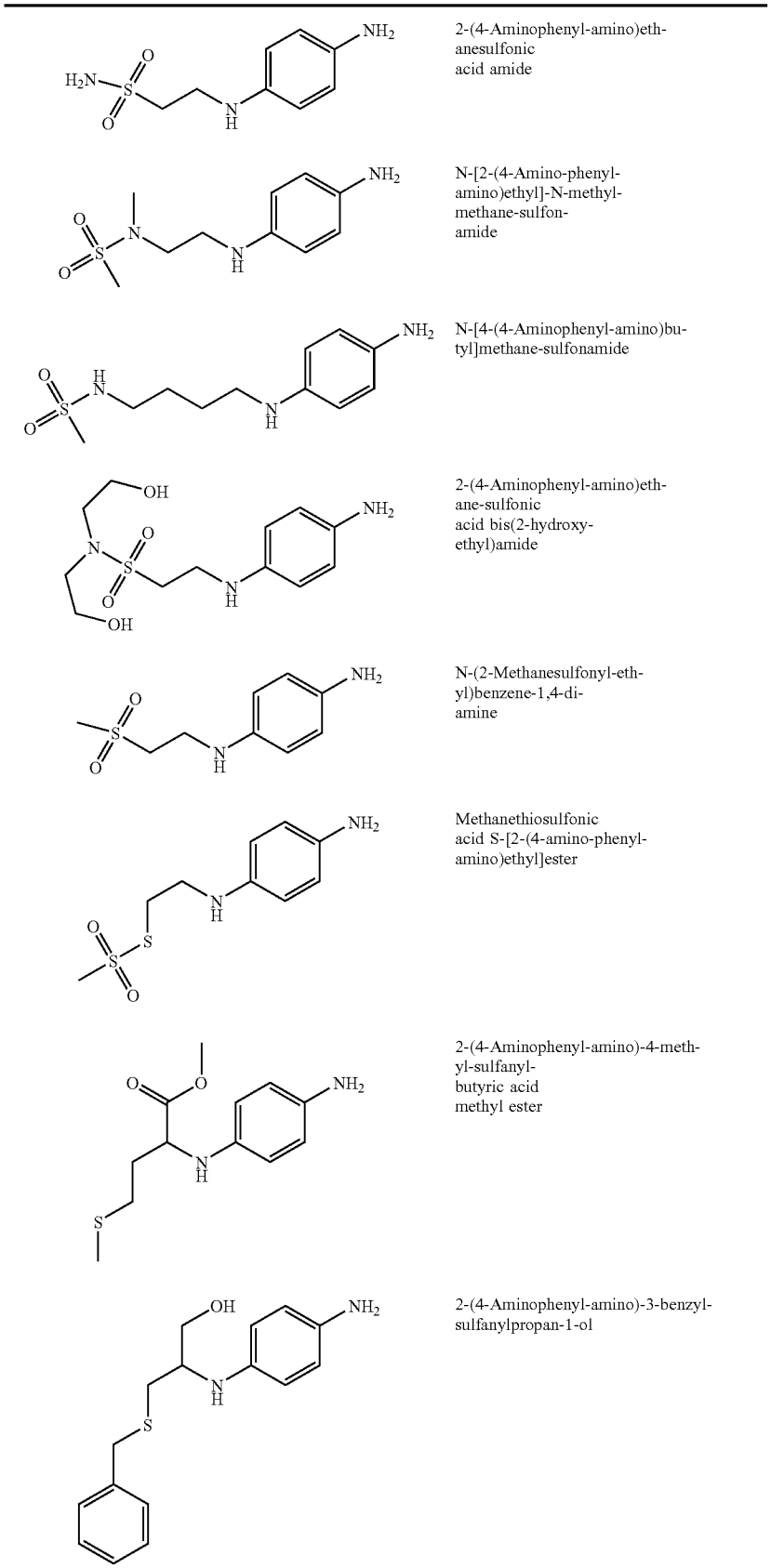

| | |
|---|---|
| | 2-(4-Aminophenyl-amino)eth-anesulfonic acid amide |
| | N-[2-(4-Amino-phenyl-amino)ethyl]-N-methyl-methane-sulfon-amide |
| | N-[4-(4-Aminophenyl-amino)bu-tyl]methane-sulfonamide |
| | 2-(4-Aminophenyl-amino)eth-ane-sulfonic acid bis(2-hydroxy-ethyl)amide |
| | N-(2-Methanesulfonyl-eth-yl)benzene-1,4-di-amine |
| | Methanethiosulfonic acid S-[2-(4-amino-phenyl-amino)ethyl]ester |
| | 2-(4-Aminophenyl-amino)-4-meth-yl-sulfanyl-butyric acid methyl ester |
| | 2-(4-Aminophenyl-amino)-3-benzyl-sulfanylpropan-1-ol |

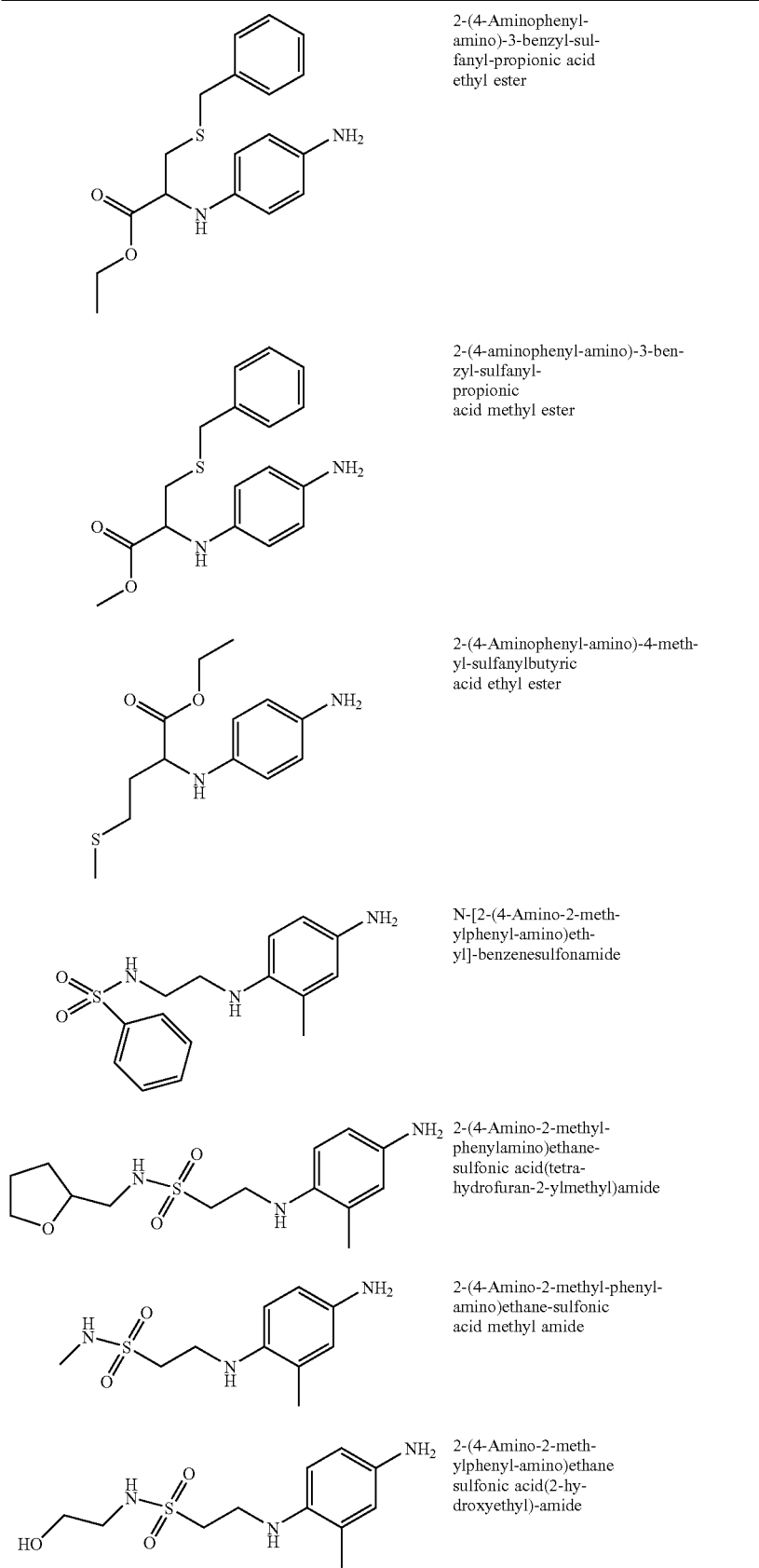

| Structure | Name |
|---|---|
| | 2-(4-Aminophenyl-amino)-3-benzyl-sulfanyl-propionic acid ethyl ester |
| | 2-(4-aminophenyl-amino)-3-benzyl-sulfanyl-propionic acid methyl ester |
| | 2-(4-Aminophenyl-amino)-4-methyl-sulfanylbutyric acid ethyl ester |
| | N-[2-(4-Amino-2-methylphenyl-amino)ethyl]-benzenesulfonamide |
| | 2-(4-Amino-2-methyl-phenylamino)ethane-sulfonic acid(tetrahydrofuran-2-ylmethyl)amide |
| | 2-(4-Amino-2-methyl-phenyl-amino)ethane-sulfonic acid methyl amide |
| | 2-(4-Amino-2-methylphenyl-amino)ethane sulfonic acid(2-hydroxyethyl)-amide |

-continued

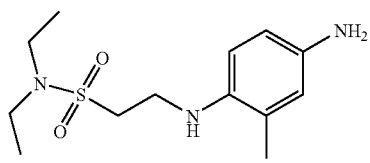
2-(4-Amino-2-methyl-phenyl-amino)ethane sulfonic acid diethylamide

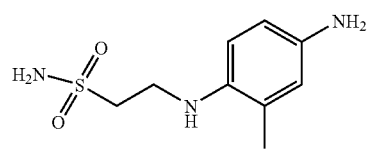
2-(4-Amino-2-methyl-phenyl-amino)ethane-sulfonic acid amide

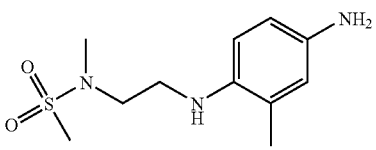
N-[2-(4-Amino-2-methyl-phenylamino)ethyl]-N-methyl-methane-sulfonamide

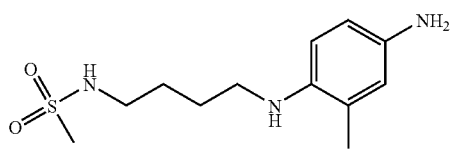
N-[4-(4-Amino-2-methyl-phenyl-amino)butyl]-methanesulfonamide

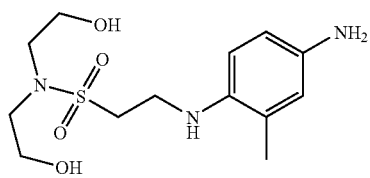
2-(4-Amino-2-methyl-phenyl-amino)ethane sulfonic acid bis(2-hydroxy-ethyl)amide

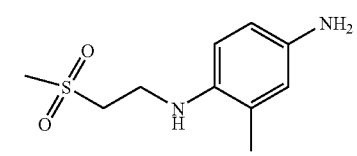
N-1-(2-Methane-sulfonyl-ethyl)-2-methyl-benzene-1,4-diamine

Methanethiosulfonic acid S-[2-(4-amino-2-methylphenyl-amino)ethyl]ester

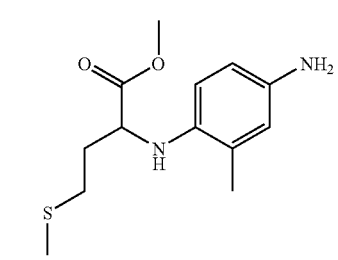
2-(4-Amino-2-methyl-phenyl-amino)-4-methyl-sulfanylbutyric acid methyl ester

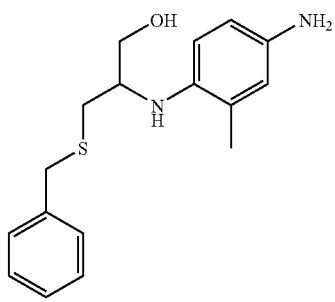 2-(4-Amino-2-methyl-phenyl-amino)-3-benzyl-sulfanyl-propan-1-ol

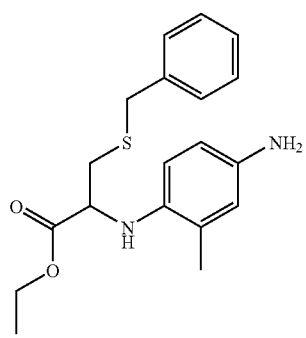 2-(4-Amino-2-methyl-phenyl-amino)-3-benzyl-sulfanyl-propionic acid ethyl ester

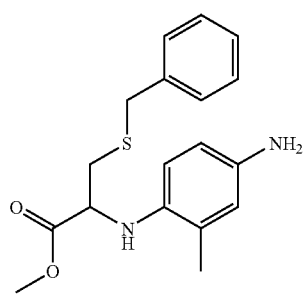 2-(4-Amino-2-methylphenylamino)-3-benzyl-sulfanyl-propionic acid methyl ester

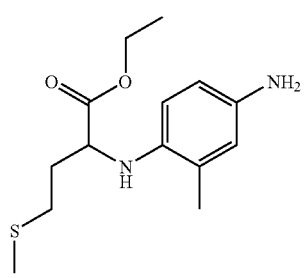 2-(4-Amino-2-methyl-phenyl-amino)-4-methyl-sulfanylbutyric acid ethyl ester

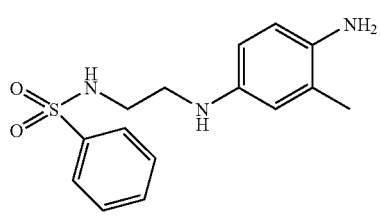 N-[2-(4-Amino-3-methyl-phenyl-amino)ethyl]-benzene-sulfonamide

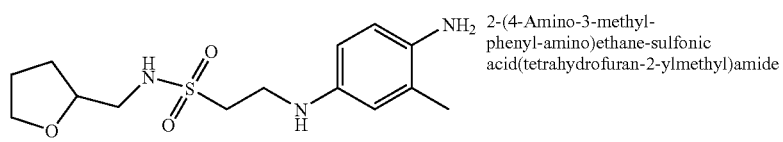 2-(4-Amino-3-methyl-phenyl-amino)ethane-sulfonic acid(tetrahydrofuran-2-ylmethyl)amide -continued

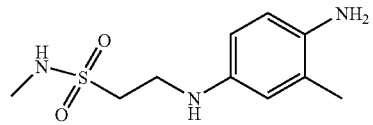 2-(4-Amino-3-methyl-phenyl-amino)ethane-sulfonic acid methylamide

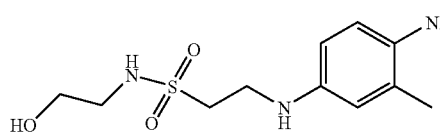 2-(4-Amino-3-methyl-phenylamino)ethanesulfonic acid (2-hydroxyethyl)amide

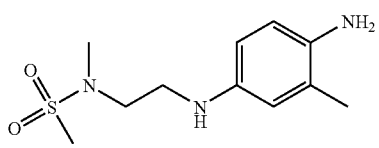 N-[2-(4-Amino-3-methyl-phenyl-amino)ethyl]-N-methyl-methanesulfonamide

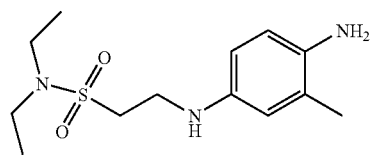 2-(4-Amino-3-methyl-phenyl-amino)ethane sulfonic acid diethyl-amide

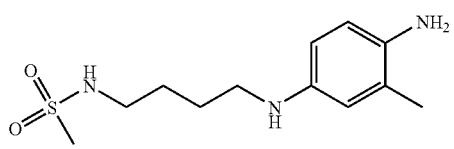 N-[4-(4-Amino-3-methyl-phenyl-amino)butyl]-methane-sulfonamide

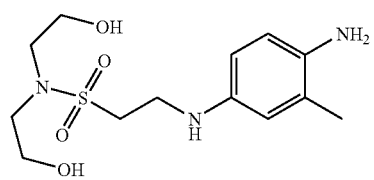 2-(4-Amino-3-methyl-phenyl-amino)ethane-sulfonic acid bis(2-hydroxyethyl)amide

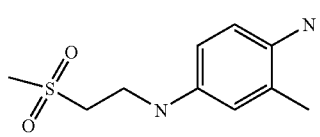 N-4-(2-Methane-sulfonyl-ethyl)-2-methyl-benzene-1,4-diamine

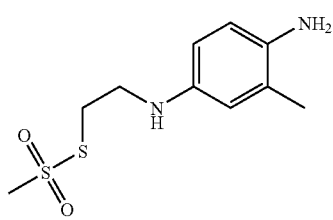 Methanethiosulfonic acid S-[2-(4-amino-3-methyl-phenyl-amino)ethyl]ester

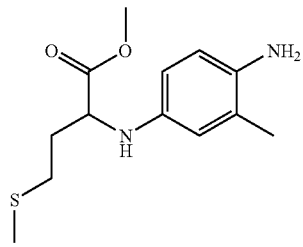
2-(4-Amino-3-methyl-phenyl-amino)-4-methyl-sulfanylbutyric acid methyl ester
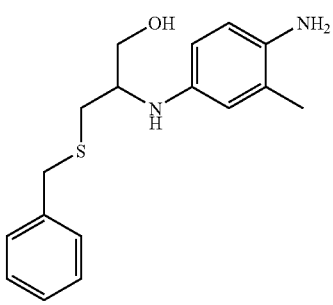
2-(4-Amino-3-methyl-phenyl-amino)-3-benzylsulfanylpropan-1-ol
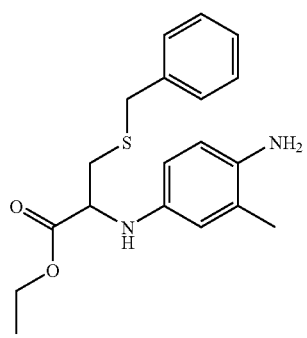
2-(4-Amino-3-methyl-phenyl-amino)-3-benzyl-sulfanyl-propionic acid ethyl ester
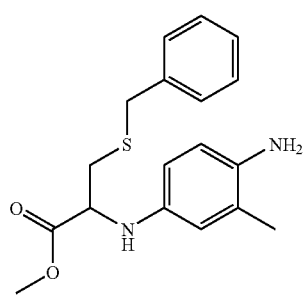
2-(4-amino-3-methyl-phenyl-amino)-3-benzyl-sulfanyl-propionic acid methyl ester
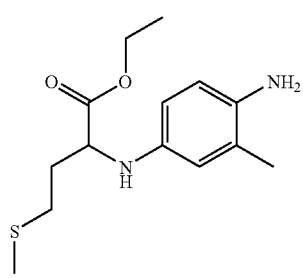
2-(4-Amino-3-methyl-phenyl-amino)-4-methyl-sulfanylbutyric acid ethyl ester By way of non-limiting example, the addition salts of the oxidation bases and couplers that may be used in the context of the present disclosure can be chosen, for example, from acid addition salts, such as the hydrochlorides, hydrobromides, sulfates, citrates, succinates, tartrates, lactates, tosylates, benzenesulfonates, phosphates, and acetates.

The compounds of formula (I) according to the present disclosure may be prepared, for example, according to processes that comprise the following:
- nucleophilic substitution of the halogen in the para position in the para-halonitrobenzene derivative with a primary amine of formula $R_1XRNH_2$ in the presence of a base ($R_1$, X, and R being as defined above), and
- reduction of the nitro functional group of the compound obtained into an amine functional group, to obtain the compound of formula (I).

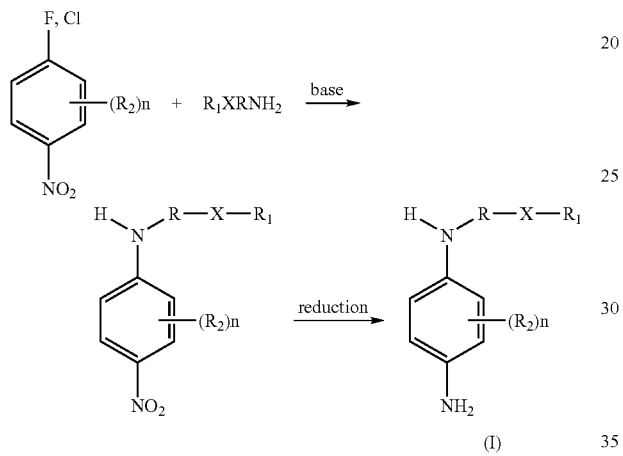

The first step of the synthesis is described in the reviews *Synthesis* 1990 (12), 1147-1148 and *Synth. Commun.* 1990, 20 (22), 3537-3545. The second step is an art-recognized reduction step, which can be performed, for example, by a hydrogenation reaction via heterogeneous catalysis in the presence of Pd/C, Pd(II)/C, or Raney Ni, or by a reduction reaction with a metal, for example with zinc, iron, tin, etc. (*Advanced Organic Chemistry*, 4th edition, 1992, J. March, Wiley Interscience; *Reduction in Organic Chemistry*, M. Hudlicky, 1983, Ellis Honwood series Chemical Science).

The present disclosure also relates to nitro compounds of formula (II) and processes for preparing the secondary para-phenylenediamine compounds of formula (I), which comprise a reduction of the corresponding nitro compound, wherein the corresponding nitro compound is a compound of formula (I) in which the amino group para to the group $NHRXR_1$ is replaced with a nitro group.

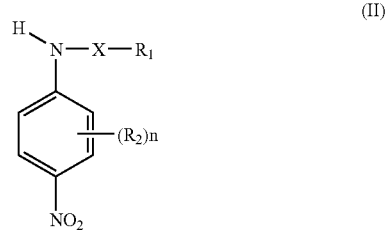

The present disclosure also relates to the use of compounds of formula (I), and the addition salts thereof, for the oxidation dyeing of keratin fibers such as hair:

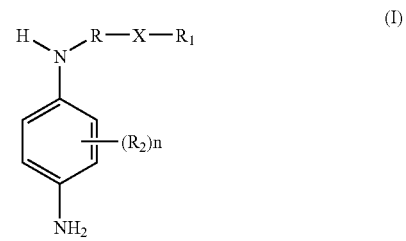

wherein:
- X is chosen from $SO_2$ and sulfur;
- if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
- if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
- $R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;
- $R_2$ is chosen from hydrogen, halogen atoms, and radicals chosen from alkyl, alkoxy, alkoxyalkyl, hydroxyalkoxy, monohydroxyalkyl, and polyhydroxyalkyl; and
- n is an integer ranging from 1 to 4;

with the exception of the following compounds:

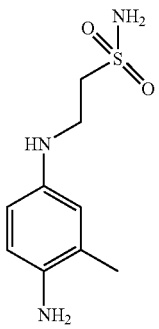
2-(4-Amino-3-methylphenyl-amino)ethanesulfonamide

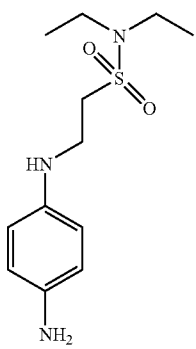
2-(4-Aminophenylamino)-ethanesulfonic acid diethylamide

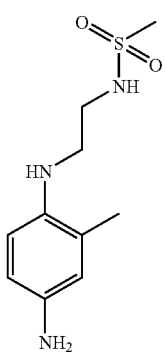
N-[2-(4-Amino-2-methyl-phenylamino)ethyl]methane-sulfonamide

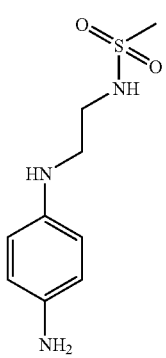
N-[2-(4-Aminophenylamino)-ethyl]methanesulfonamide

The present disclosure also relates to cosmetic compositions for dyeing fibers, for example human keratin fibers such as hair, comprising, in a medium that is suitable for dyeing, at least one compound of formula (I), and the addition salts thereof:

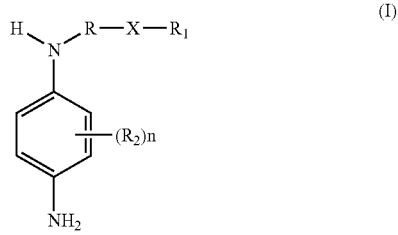

wherein:

X is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4;

with the exception of the following compounds:

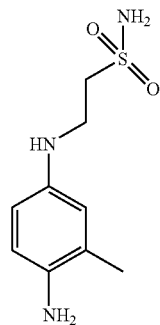 2-(4-Amino-3-methylphenyl-amino)eth-anesulfonamide

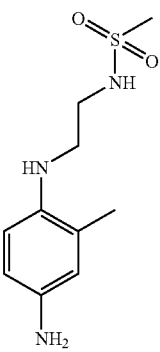 N-[2-(4-Amino-2-methyl-phenyl-amino)ethyl]methane-sulfonamide

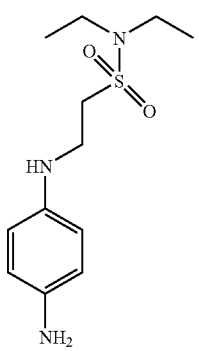 2-(4-Aminophenyl-amino)eth-anesulfonic acid diethylamide

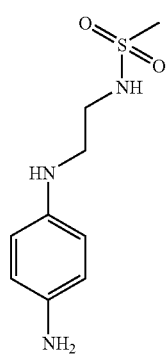 N-[2-(4-Aminophenyl-amino)eth-yl]methane sulfonamide

In one embodiment, the compounds of formula (I) are chosen from:

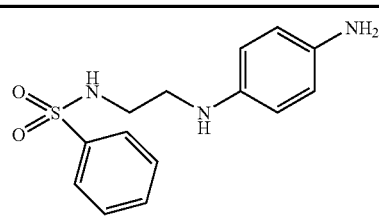 N-[2-(4-Aminophenyl-amino)-eth-yl]benzenesulfonamide

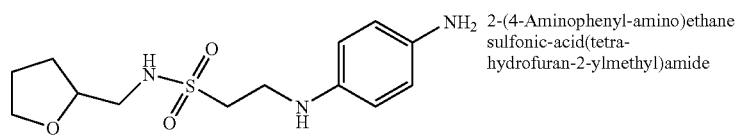 2-(4-Aminophenyl-amino)ethane sulfonic-acid(tetra-hydrofuran-2-ylmethyl)amide

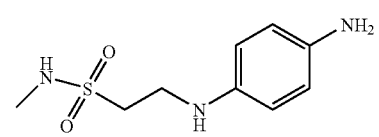 2-(4-Aminophenyl-amino)eth-anesulfonic acid methylamide

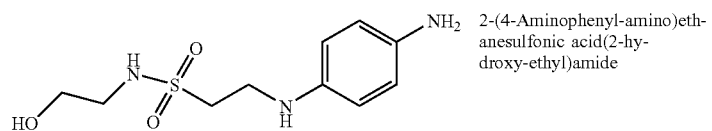 2-(4-Aminophenyl-amino)eth-anesulfonic acid(2-hydroxy-ethyl)amide

| Compound | Name |
|---|---|
| | N-[2-(4-Aminophenyl-amino)ethyl]methane sulfonamide |
| | 2-(4-Aminophenyl-amino)ethane sulfonic acid diethylamide |
| | 2-(4-Aminophenyl-amino)ethanesulfonic acid amide |
| | N-[2-(4-Aminophenyl-amino)ethyl]-N-methylmethane sulfonamide |
| | N-[4-(4-Aminophenyl-amino)butyl]methanesulfonamide |
| | 2-(4-Aminophenyl-amino)ethane sulfonic acid bis(2-hydroxy-ethyl)amide |
| | N-(2-Methane sulfonyl-ethyl)benzene-1,4-diamine |
| | Methanethio sulfonic acid S-[2-(4-aminophenyl amino)ethyl]ester |
| | Sulfuric acid mono[2-(4-aminophenyl amino)ethyl]ester |
| | Thiosulfuric acid S-[2-(4-amino phenylamino)ethyl]ester |

-continued
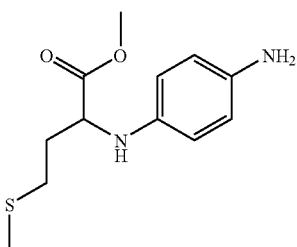
2-(4-Aminophenyl-amino)-4-methyl sulfanylbutyric acid methyl ester
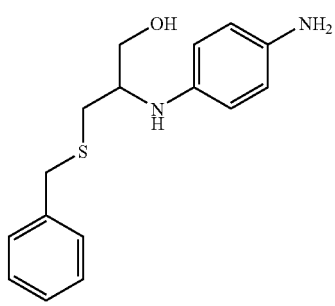
2-(4-Aminophenyl-amino)-3-benzyl-sulfanylpropan-1-ol
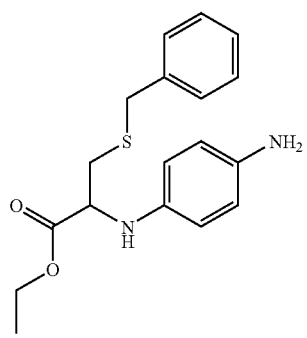
2-(4-Aminophenyl-amino)-3-benzyl sulfanylpropionic acid ethyl ester
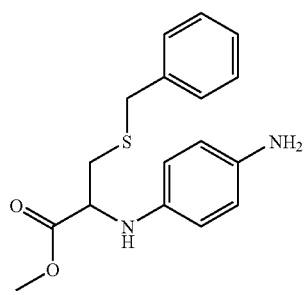
2-(4-aminophenyl-amino)-3-benzyl sulfanylpropionic acid methyl ester
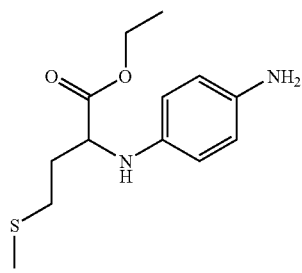
2-(4-Aminophenyl-amino)-4-methyl sulfanylbutyric acid ethyl ester

| | |
|---|---|
| 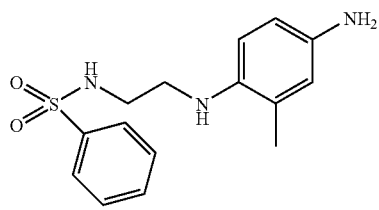 | N-[2-(4-Amino-2-methyl-phenylamino)-ethyl]benzenesulfonamide |
| 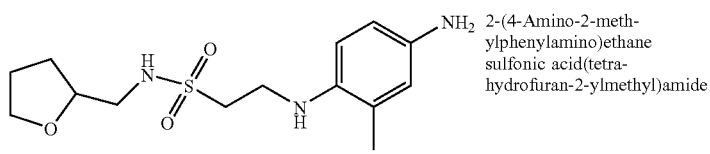 | 2-(4-Amino-2-methylphenylamino)ethane sulfonic acid(tetrahydrofuran-2-ylmethyl)amide |
| 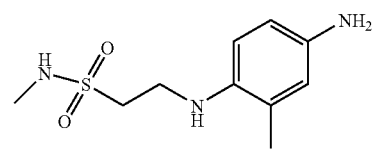 | 2-(4-Amino-2-methylphenylamino)ethane-sulfonic acid methylamide |
| 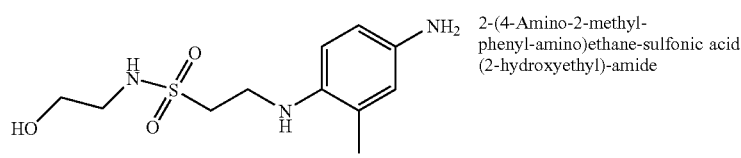 | 2-(4-Amino-2-methyl-phenyl-amino)ethane-sulfonic acid (2-hydroxyethyl)-amide |
| 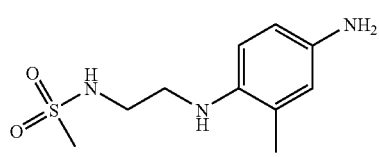 | N-[2-(4-Amino-2-methyl-phenylamino)-ethyl]-methanesulfonamide |
| 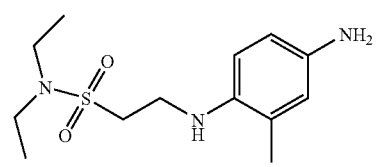 | 2-(4-Amino-2-methylphenyl-amino)ethane-sulfonic acid diethylamide |
| 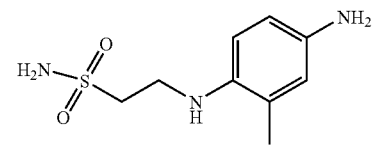 | 2-(4-Amino-2-methyl-phenylamino)-ethane-sulfonic acid amide |
| 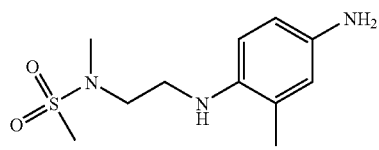 | N-[2-(4-Amino-2-methylphenyl-amino)-ethyl]-N-methyl-methane-sulfonamide |
| 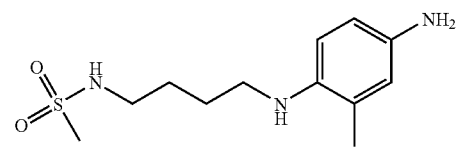 | N-[4-(4-Amino-2-methyl-phenylamino)-butyl]-methanesulfonamide |

-continued

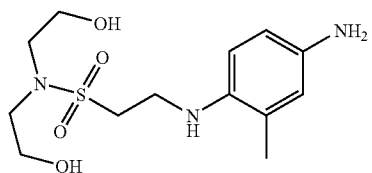 2-(4-Amino-2-methylphenyl-amino)ethane-sulfonic acid bis(2-hydroxyethyl)-amide

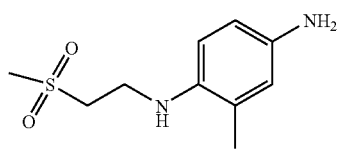 N-1-(2-Methanesulfonyl-ethyl)-2-methylbenzene-1,4-diamine

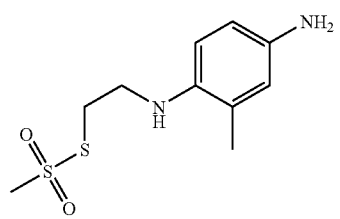 Methanethiosulfonic acid S-[2-(4-amino-2-methyl-phenylamino)ethyl]ester

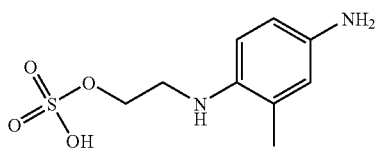 Sulfuric acid mono[2-(4-amino-2-methylphenyl-amino)ethyl]ester

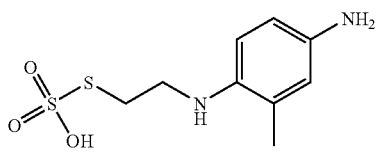 Thiosulfuric acid S-[2-(4-amino-2-methyl-yl-phenylamino)ethyl]ester

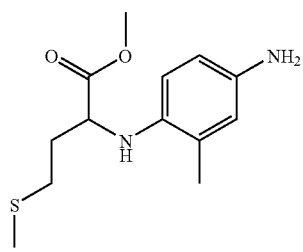 2-(4-Amino-2-methyl-phenylamino)-4-methylsulfanylbutyric acid methyl ester

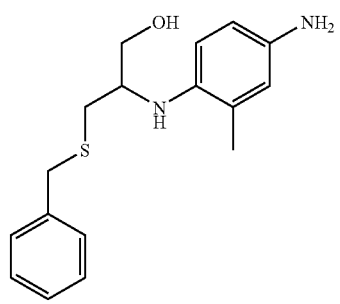 2-(4-Amino-2-methyl-phenyl-amino)-3-benzyl-sulfanyl-propan-1-ol

-continued

| | |
|---|---|
| 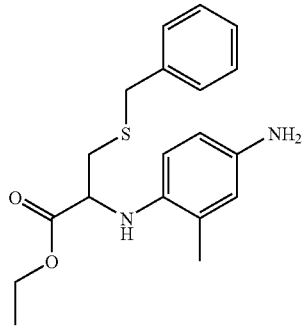 | 2-(4-Amino-2-methyl-phenyl-amino)-3-benzyl-sulfanyl-propionic acid ethyl ester |
| 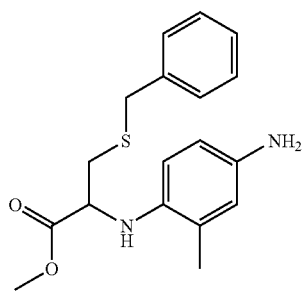 | 2-(4-Amino-2-methyl-phenylamino)-3-benzyl-sulfanyl-propionic acid methyl ester |
| 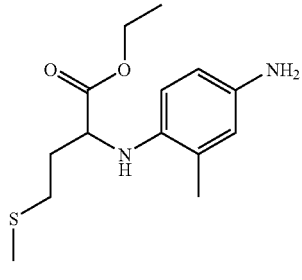 | 2-(4-Amino-2-methyl-phenyl-amino)-4-methyl-sulfanylbutyric acid ethyl ester |
| 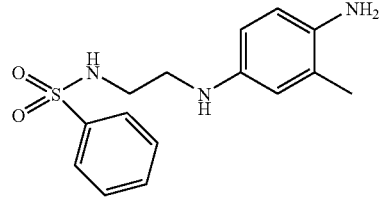 | N-[2-(4-Amino-3-methyl-phenyl-amino)ethyl]-benzenesulfonamide |
| 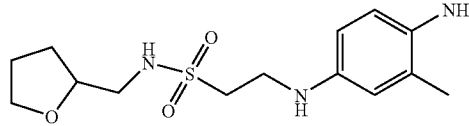 | 2-(4-Amino-3-methylphenyl amino)ethane sulfonic acid (tetrahydrofuran-2-yl-methyl)amide |
| 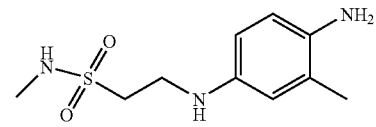 | 2-(4-Amino-3-methyl-phenyl-amino)ethane-sulfonic acid methylamide |
| 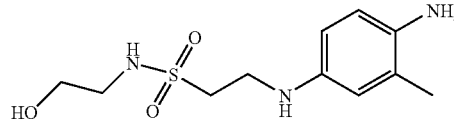 | 2-(4-Amino-3-methylphenyl-amino)ethane-sulfonic acid(2-hydroxy-ethyl)-amide |

-continued

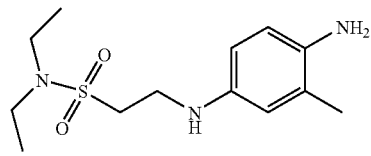 2-(4-Amino-3-methylphenyl amino)ethane sulfonic acid diethylamide

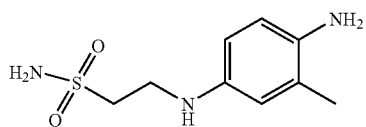 2-(4-Amino-3-methyl-phenyl-amino)ethane sulfonic acid amide

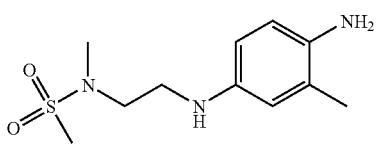 N-[2-(4-Amino-3-methylphenyl amino)ethyl]-N-methylmethane-sulfonamide

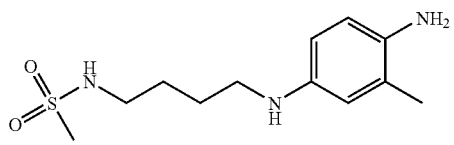 N-[4-(4-Amino-3-methyl-phenylamino)-butyl]methane-sulfonamide

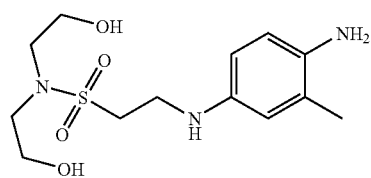 2-(4-Amino-3-methylphenyl-amino)ethane-sulfonic acid bis(2-hydroxyethyl)amide

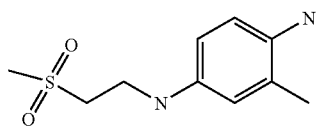 N-4-(2-Methane sulfonyl-ethyl)-2-methyl-benzene-1,4-diamine

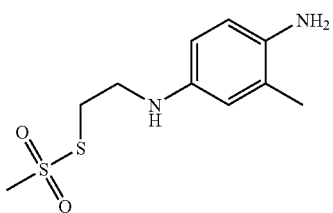 Methanethio sulfonic acid S-[2-(4-amino-3-methylphenyl amino)ethyl]ester

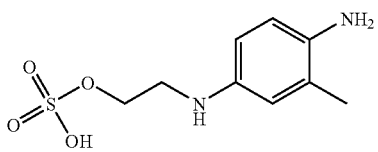 Sulfuric acid mono[2-(4-amino-3-methylphenyl-amino)ethyl]ester

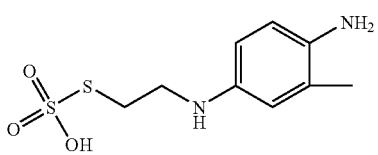 Thiosulfuric acid S-[2-(4-amino-3-methylphenyl amino)ethyl]ester

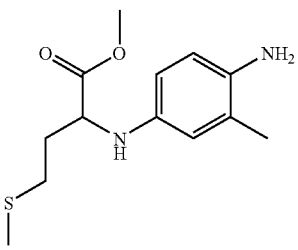
2-(4-Amino-3-methyl-phenylamino)-4-methylsulfanyl butyric acid methyl ester
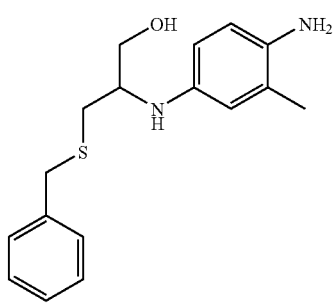
2-(4-Amino-3-methyl-phenyl-amino)-3-benzyl-sulfanyl-propan-1-ol
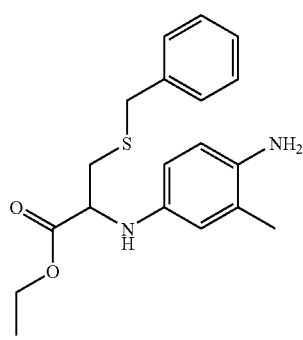
2-(4-Amino-3-methyl-phenyl-amino)-3-benzylsulfanyl propionic acid ethyl ester
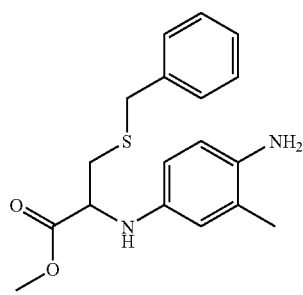
2-(4-Amino-3-methylphenyl amino)-3-benzylsulfanyl-propionic acid methyl ester
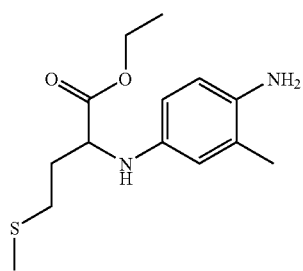
2-(4-Amino-3-methyl-phenyl-amino)-4-methyl-sulfanylbutyric acid ethyl ester

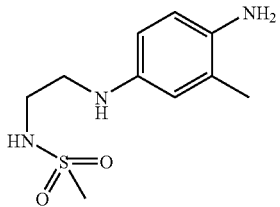 N-[2-(4-Amino-3-methylphenyl amino)ethyl]methanesulfonamide

In at least one embodiment, the compound of formula (I) may be present in an amount ranging from 0.0001% to 20% by weight, such as from 0.005% to 6% by weight, relative to the total weight of the composition.

The medium that is suitable for dyeing may consist of water or may comprise a mixture of water and at least one organic solvent, chosen for instance from branched and unbranched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether, diethylene glycol monoethyl ether, and glycerol; aromatic alcohols, for instance benzyl alcohol and phenoxyethanol; and mixtures thereof.

When present, the at least one organic solvent may be present in an amount ranging from 1% to 40% by weight, such as from 5% to 30% by weight, relative to the total weight of the dye composition.

The cosmetic compositions in accordance with the present disclosure may also comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins, and provitamins.

When present, each adjuvant may be present in an amount ranging from 0.01% to 20% by weight relative to the weight of the composition.

A person skilled in the art will take care to select optional additional compound(s) such that the beneficial properties intrinsically associated with the oxidation dye compositions in accordance with the present disclosure are not, or are not substantially, adversely affected by the envisaged addition(s).

The compositions according to the present disclosure may also comprise at least one oxidation coupler. Among the oxidation couplers that may be used, non-limiting mention may be made of meta-phenylenediamines, meta-aminophenols, meta-diphenols, naphthalene-based couplers, heterocyclic couplers, and the addition salts thereof.

Non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, and the addition salts thereof.

When present, the at least one oxidation coupler may be present in an amount ranging from 0.0001% to 20% by weight, for example from 0.005% to 6% by weight, relative to the total weight of the composition.

The compositions according to the present disclosure may also comprise at least one additional oxidation base (dye precursor) other than compounds of formula (I).

The additional oxidation bases may be chosen, for example, from para-phenylenediamines, bis(phenyl)alkylenediamines, para-aminophenols, ortho-amino phenols, heterocyclic bases, and the addition salts thereof.

Among the para-phenylenediamines, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, and the acid addition salts thereof.

Among the para-phenylenediamines mentioned above, further non-limiting examples include para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bis(phenyl)alkylenediamines, non-limiting mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)

ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Among the para-aminophenols, non-limiting mention may be made, by way of example, of para-aminophenol, 4-amino-2-methylphenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol, bis(5'-amino-2'-hydroxy)phenylmethane, and the acid addition salts thereof.

Among the ortho-aminophenols, non-limiting mention may be made, by way of example, of 2-aminophenol, 2-amino-5-methylphenol, 2-amino-6-methylphenol, 5-acetamido-2-aminophenol, and the acid addition salts thereof.

Among the heterocyclic bases, non-limiting mention may be made, by way of example, of pyridine derivatives, pyrimidine derivatives, and pyrazole derivatives.

Among the pyridine derivatives, non-limiting mention may be made of the compounds described, for example, in British Patent Nos. GB 1,026,978 and GB 1,153,196, as well as 2,5-diaminopyridine, 2-(4-methoxyphenyl)amino-3-aminopyridine, 3,4-diaminopyridine, and the acid addition salts thereof.

Other pyridine oxidation bases that may be used according to the present disclosure include, but are not limited to, the 3-aminopyrazolo[1,5-a]pyridine oxidation bases and the addition salts thereof described, for example, in French Patent Application No. FR 2,801,308. Non-limiting examples that may be mentioned include pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyridine-6-ol; 3-aminopyrazolo[1,5-a]pyrid-7-ol; and the acid addition salts thereof.

Among the pyrimidine derivatives, non-limiting mention may be made of the compounds described, for example, in German Patent No. DE 2,359,399, Japanese Patent Nos. JP 88-169,571 and JP 05,63,124, European Patent No. EP 0,770,375, and International Patent Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6diaminopyrimidine, 2,5,6-triaminopyrimidine, the addition salts thereof, and the tautomeric forms thereof, when a tautomeric equilibrium exists.

Among the pyrazole derivatives, non-limiting mention may be made of the compounds described in German Patent Nos. DE 3,843,892 and DE 4,133,957, International Patent Publication Nos. WO 94/08969 and WO 94/08970, French Patent Application No. FR-A-2,733,749, and German Patent Application No. DE 195,43,988, such as 4,5-diamino-1-methylpyrazole, 4,5-diamino-1-(P-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

When present, the at least one oxidation base may be present in an amount ranging from 0.0001% to 20% by weight, for example from 0.005% to 6% by weight, relative to the total weight of the composition.

The addition salts of the oxidation bases and couplers that may be used in the context of the present disclosure may be chosen, for example, from the acid addition salts such as the hydrochlorides, hydrobromides, sulfates, citrates, succinates, tartrates, lactates, tosylates, benzenesulfonates, phosphates, and acetates.

The dye compositions in accordance with the present disclosure may also comprise at least one direct dye, which may be chosen, for example, from neutral, acidic, and cationic nitrobenzene dyes; neutral, acidic, and cationic azo direct dyes; neutral, acidic, and cationic quinone dyes, such as anthraquinone direct dyes; azine direct dyes; triarylmethane direct dyes; indoamine direct dyes; and natural direct dyes. In one embodiment, the compositions according to the present disclosure comprise at least one dye chosen from cationic direct dyes and natural direct dyes.

Among the cationic direct dyes that may be used according to the present disclosure, non-limiting mention may be made of the cationic azo direct dyes described in International Patent Publication Nos. WO 95/15144 and WO 95/01772, and European Patent Application EP 714,954.

Among these compounds, further non-limiting mention may be made of the following dyes:

1,3-dimethyl-2-[[4-(dimethylamino)phenyl]azo]-1H-imidazolium chloride;

1,3-dimethyl-2-[(4-aminophenyl)azo]-1H-imidazolium chloride; and 1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts and decoctions comprising these natural dyes, for example henna-based poultices and extracts.

When present, the at least one direct dye may be present in an amount ranging from 0.001% to 20% by weight, for example from 0.005% to 10% by weight, relative to the total weight of the ready-to-use composition.

Ready-to-use dye compositions may be obtained by adding at least one oxidizing agent. The oxidizing agents conventionally used for the oxidation dyeing of keratin fibers include, for example, hydrogen peroxide; urea peroxide; alkali metal bromates; persalts such as perborates and persulfates; peracids; and oxidase enzymes, among which non-limiting mention may be made of peroxidases, two-electron oxidoreductases such as uricases, and four-electron oxygenases, for instance laccases. In one embodiment, the ready-to-use compositions comprise hydrogen peroxide.

The pH of the dye compositions in accordance with the present disclosure may range from 3 to 12, for example from 5 to 11. It may be adjusted to the desired value using acidifying or basifying agents usually used in the dyeing of keratin fibers, or alternatively using standard buffer systems.

Among the acidifying agents that may be used, non-limiting mention may be made, for example, of mineral and organic acids other than carboxylic diacids, for instance hydrochloric acid, orthophosphoric acid, sulfuric acid, carboxylic acids, such as acetic acid, tartaric acid, citric acid and lactic acid, and sulfonic acids.

Among the basifying agents that may be used, non-limiting mention may be made, for example, of aqueous ammonia, alkali metal carbonates, alkanolamines such as monoethanolamine, diethanolamine, triethanolamine, and derivatives thereof, sodium hydroxide, potassium hydroxide, and the compounds of formula (III):

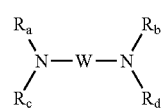

(III)

wherein:
  W is chosen from propylene residues optionally substituted with a hydroxyl group or a $C_1$-$C_4$ alkyl radical; and
  $R_a$, $R_b$, $R_c$, and $R_d$, which may be identical or different, are chosen from hydrogen, and $C_1$-$C_4$ alkyl and $C_1$-$C_4$ hydroxyalkyl radicals.

The dye compositions according to the present disclosure may be in various forms, such as in the form of liquids, creams or gels, or in any other form that is suitable for dyeing keratin fibers, such as hair.

The present disclosure also relates to processes in which the compositions described herein are applied to the fibers and the color is developed using an oxidizing agent. The color may be developed at acidic, neutral or alkaline pH. The oxidizing agent may be added to the compositions of the present disclosure just at the time of use. It may also be used starting with an oxidizing composition comprising it, which is applied simultaneously with or sequentially to the fibers at the time of application of the dye compositions of the present disclosure.

In one embodiment, a composition in accordance with the present disclosure is mixed, for example, at the time of use, with a composition comprising, in a medium that is suitable for dyeing, at least one oxidizing agent, this oxidizing agent being present in an amount that is sufficient to develop a coloration. The mixture obtained is then applied to keratin fibers. After leaving it to act for a period of time ranging from 3 to 50 minutes, for example from 5 to 30 minutes, the keratin fibers are rinsed, washed with shampoo, rinsed again, and then dried.

The oxidizing compositions may also comprise various adjuvants conventionally used in hair dye compositions and as defined above.

The pH of the oxidizing compositions comprising the oxidizing agent may be such that, after mixing with a dye composition in accordance with the present disclosure, the pH of the resulting composition applied to the keratin fibers ranges, for example, from 3 to 12, such as from 5 to 11. It may be adjusted to the desired value by means of acidifying or basifying agents usually used in the dyeing of keratin fibers and as defined above.

The ready-to-use compositions that are finally applied to the keratin fibers may be in various forms, such as in the form of liquids, creams or gels, or in any other form that is suitable for dyeing keratin fibers, for example hair.

The present disclosure also relates to the use of the cosmetic compositions described herein comprising, in a medium that is suitable for dyeing, at least one compound of formula (I) for dyeing fibers, for example keratin fibers such as hair.

The present disclosure also relates to multi-compartment devices or dyeing kits, in which at least one first compartment comprises at least one dye composition described herein and at least one second compartment comprises a least one oxidizing composition. This kit may be equipped with a device for applying the desired mixture to the hair, such as the devices described in French Patent No. FR-2,586,913.

Using these kits, it is possible to dye keratin fibers via processes that include mixing at least one dye composition in accordance with the present disclosure with a least one oxidizing agent as defined above, and applying the mixture obtained to the keratin fibers for a time that is sufficient to develop the desired coloration.

The present disclosure may be understood more clearly with the aid of the non-limiting examples that follow, which constitute various embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

The examples that follow serve to illustrate the invention without, however, being limiting in nature.

EXAMPLES

Example 1

Synthesis of N-{2-[(4-aminophenyl)amino]ethyl}benzenesulfonamide (3)

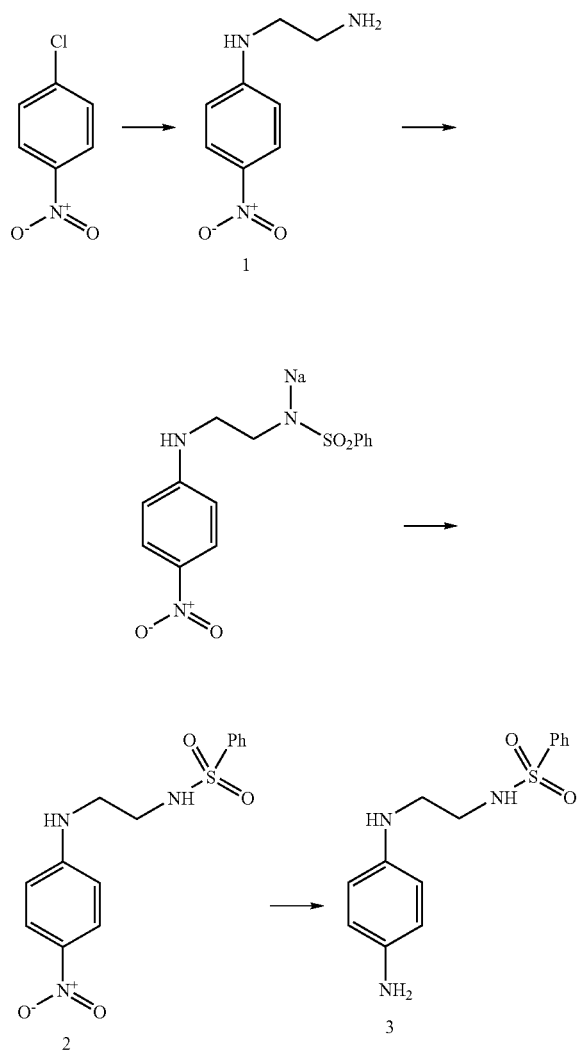

Step 1: Preparation of N-(2-aminoethyl)-N-(4-aminophenyl)amine (1)

Para-chloronitrobenzene (181.6 g, 1.152 mol) was dissolved in 180 mL of pyridine with warming. This solution was poured dropwise over 75 minutes into a round-bottomed flask containing ethylenediamine (359.4 g, 4.608 mol) with stirring. The mixture was heated at 90° C. for 2 hours in a boiling water bath. The solution was poured into 3 L of water with stirring. The mixture was allowed to cool to room temperature and the precipitate was filtered off by suction and then reslurried twice in water. The crude product was taken up in 1200 mL of 2N hydrochloric acid for 1 hour. The hydrochloride was filtered off and dissolved in 2 L of water at 95° C., and the insoluble matter was again filtered off. The aqueous solution of hydrochloride obtained was poured while hot into a beaker, at about 80° C. 120 mL of 0.5N sodium hydroxide were added to pH=12. After cooling, the crystalline product was filtered off by suction, re-slurried in water, and then re-crystallized from absolute ethanol. 155 g of orange-colored solids with a melting point of 149° C. were isolated.

Step 2: Preparation of N-{2-[(4-nitrophenyl)amino]ethyl}benzenesulfonamide 45.3 g (0.25 mol) of N-(2-aminoethyl)-N-(4-aminophenyl)amine (1) were suspended in 200 mL of pyridine in a 500 mL round-bottomed flask. This mixture was brought to 45-50° C. and benzenesulfonyl chloride (48.6 g, 35.2 mL) was poured in over 15 minutes. The solution obtained was left for a further 90 minutes at 50° C. and then poured onto 1 kg of ice and 143 mL of concentrated hydrochloric acid with stirring. A yellow solid formed, which was filtered off by suction and then reslurried in water to give 136 g (wet) of yellow product. The product was treated with 650 mL of 1N sodium hydroxide at 85° C. This mixture was filtered while hot and the filtrate was left to cool in order to obtain a suction filtered off product. After drying, 81 g of product were obtained. This product was the corresponding sodium salt of N-{2-[(4-nitrophenyl)amino]ethyl}benzenesulfonamide and had a melting point of 170° C.

To release the sodium salt, the product (60 g) was dissolved in 300 mL of 1N sodium hydroxide at 85° C. and, after filtering while hot, the filtrate was neutralized with 5N hydrochloric acid to pH=3. The crystalline product was filtered off by suction, washed with water, and then dried over $P_2O_5$ to give 50 g of expected product with a melting point of 171° C.

Step 3: Preparation of N-{2-[(4-aminophenyl)amino]ethyl}benzenesulfonamide (3)

A mixture of zinc powder (2 g) and ammonium chloride (0.2 g) in 22 ml of a water/ethanol mixture (1/1) was refluxed in a boiling-water bath. The derivative N-{2-[(4nitrophenyl)amino]ethyl}benzenesulfonamide (2) (3 g, 9 mmol) was added in portions and heating was continued until the reaction medium decolorized. The mixture was filtered while hot and the zinc was rinsed with ethanol/water solution (50/50). The filtrate crystallized rapidly. After cooling to 0° C., the solid was filtered off and then washed with water. After drying, 2.27 g of crude product with a melting point of 144° C. were obtained. 0.77 g of this crude product was recrystallized from 20 mL of water/ethanol (1/1), and the crystals obtained were dried over $P_2O_5$ and microanalysed.

|   | THEORY | FOUND |
|---|--------|-------|
| C | 57.72  | 57.90 |
| H | 5.88   | 5.90  |
| N | 14.43  | 14.22 |
| S | 10.98  | 11.02 |

The proton NMR and mass spectra were in accordance with the expected structure of the product.

Example 2

Synthesis of 2-[(4-aminophenyl)amino]-N-(tetrahydrofuran-2-ylmethyl)ethanesulfonamide dihydrochloride (11)

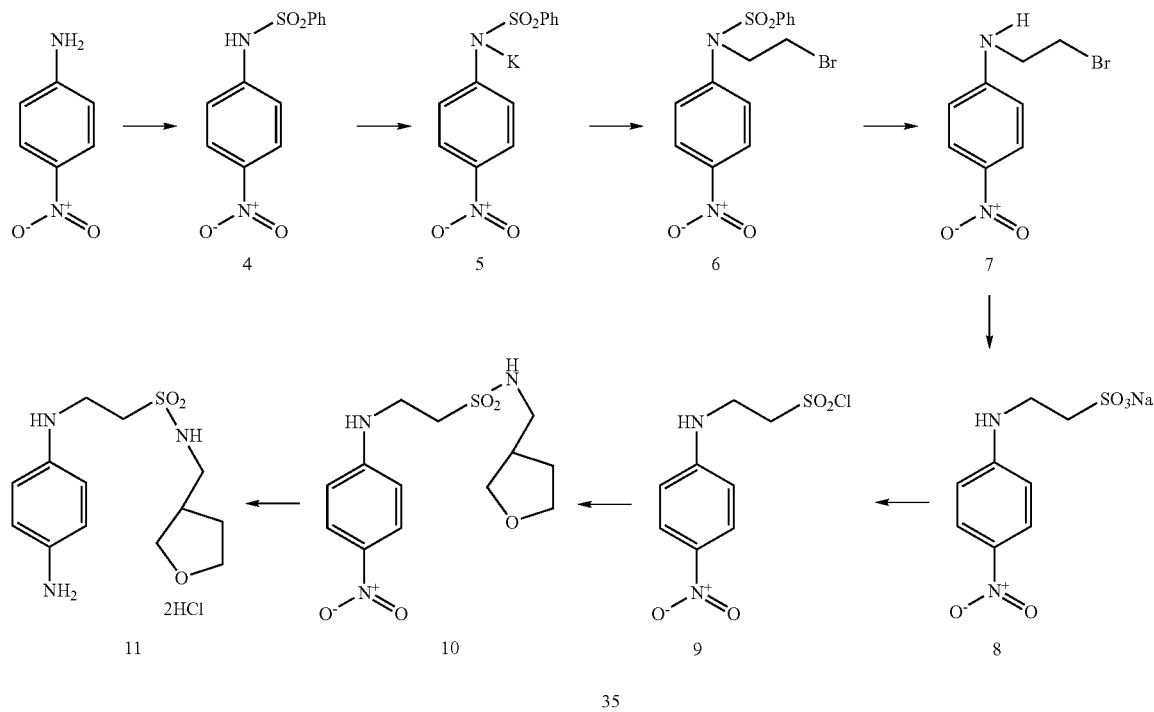

Step 1: Preparation of N-(4-nitrophenyl)benzenesulfonamide (4)

A solution of p-nitroaniline (1 kg, 7.245 mol) in pyridine (3.6 L) was brought to 45° C. Benzenesulfonyl chloride (1.41 kg, 8 mol) was poured in over 70 minutes, while maintaining the temperature ranging from 45 to 50° C. After 1 hour at 50° C., the reaction medium was poured onto 8 kg of ice and 4.35 L of hydrochloric acid. A yellow precipitate formed and was filtered off by suction and then dissolved in 20 L of 0.5 N sodium hydroxide at 55° C. The insoluble matter was removed by filtration and the filtrate was then neutralized hydrochloric acid while still hot. A yellow precipitate formed and was filtered off by suction, reslurried in water, and then air-dried. 2 kg of product with a melting point of 137° C. were obtained.

Step 2: Preparation of the Potassium Salt of N-(4-nitrophenyl)benzenesulfonamide (5)

1.817 kg (6.5 mol) of N-(4-nitrophenyl)benzenesulfonamide (4) were dissolved in 4.5 L of ethanol and then heated to reflux. 470 g of potassium hydroxide (85% pure, 7.15 mol) were dissolved in 250 ml of water and this solution was added over 30 minutes to the reaction medium at about 75° C. After cooling, compound (5) crystallized. This product was filtered off by suction and washed with ethanol and then with petroleum ether. After drying, 1.85 kg of product (5) were obtained.

Step 3: Preparation of N-(2-bromoethyl)-N-(4-nitrophenyl)benzenesulfonamide (6)

1,2-Dibromoethane (2.26 kg, 12 mol) mixed with 4 L of dimethylformamide was brought to 80° C. 1.264 kg (4 mol) of the potassium salt of N-(4-nitrophenyl)benzenesulfonamide (5) was added in portions and the mixture was stirred at 90-95° C. for 4 hours. The resulting mixture was filtered while hot and a KBr salt was formed, which was washed with dimethylformamide. The filtrate was poured onto 20 kg of ice in 20 kg of water. A yellow precipitate formed, which was filtered off by suction, reslurried three times in hot 1N sodium hydroxide, and then reslurried in water to neutral pH. The crude product (1.2 kg wet) obtained was recrystallized from 3 L of acetic acid. This mixture was filtered while boiling and the filtrate was cooled to 20° C. A white precipitate formed, which was filtered off by suction, washed with acetic acid and then with petroleum ether, and then dried under vacuum. 773 g product with a melting temperature of 168° C. were isolated.

Step 4: Preparation of (2-bromoethyl)-(4-nitrophenyl)amine (7)

770 g (2 mol) of product obtained above (6) were dissolved in 3.85 L of sulfuric acid. The mixture was stirred for 1 hour at room temperature, then poured onto 20 kg of ice in 10 kg of water. A yellow precipitate formed, which was filtered off, reslurried in water to neutral pH, and left to dry. 482 g of product with a melting point of 95° C. were obtained.

Step 5: Preparation of sodium 2-[(4-nitrophenyl)amino]ethanesulfonate (8)

661 g (2.7 mol) of (2-bromoethyl)(4-nitrophenyl)amine (7) were partially dissolved in 3.7 L of 96% ethanol. At about 75-80° C., aqueous sodium sulfite solution (820 g, 6.5 mol of Na$_2$SO$_3$ in 2.4 L of water) was added. The mixture was stirred at reflux for 11 hours. The resulting mixture was filtered while boiling and the filtrate was allowed to cool. A yellow precipitate formed, which was filtered off by suction and washed with acetone. After drying, 623 g of product were isolated.

Step 6: Preparation of 2-[(4-nitrophenyl)amino]ethanesulfonyl chloride (9)

A mixture of sodium 2-[(4-nitrophenyl)amino]ethanesulfonate (8) (5.36 g, 0.02 mol), phosphorus pentachloride (4.58 g, 0.022 mol) and 50 mL of anhydrous xylene was heated at about 40-50° C. for 4 hours. After remaining at room temperature overnight, the mixture was heated for 3 hours in a boiling water bath. The resulting mixture was filtered while hot and the insoluble matter was washed three times with hot xylene. The filtrate was left to cool. A yellow solid formed, and was filtered off and reslurried in water. 2.4 g of expected product were isolated.

The results of the elemental analyses were as follows:

|   | THEORY | FOUND |
|---|---|---|
| C | 36.29 | 36.48 |
| H | 3.40 | 3.59 |
| N | 10.58 | 10.48 |
| Cl | 13.42 | 13.59 |
| S | 12.10 | 12.06 |

Step 7: Preparation of 2-[(4-nitrophenyl)amino]-N-(tetrahydrofuran-2-ylmethyl)ethanesulfonamide (10)

20 mL (0.2 mol) of tetrahydrofurfurylamine were mixed with 75 mL of ethyl acetate. 2-[(4-nitrophenyl)amino]ethanesulfonyl chloride (9) (13.2 g, 0.05 mol) was introduced, at 0° C., and the mixture was then allowed to return to room temperature overnight. The amine hydrochloride formed was filtered off and the ethyl acetate phase was extracted with 2.5N hydrochloric acid and then with water. The organic phase was stripped off and evaporated to dryness under vacuum to give 13.5 g of product in the form of an oil.

Step 8: Preparation of 2-[(4-aminophenyl)amino]-N-(tetrahydrofuran-2-ylmethyl)ethanesulfonamide dihydrochloride (11)

A mixture of zinc powder (3.8 g), ammonium chloride (0.22 g), water (0.75 mL), and 96% ethanol (10 mL) was refluxed in a boiling water bath. The derivative 2-[(4-nitrophenyl)amino]-N-(tetrahydrofuran-2-ylmethyl)ethanesulfonamide (10) (2.52 g, 7.6 mmol) was added in portions and heating was continued until the reaction medium decolorized. The resulting mixture was filtered while boiling and the filtrate was recovered onto 12 mL of ethanol and 1.5 mL of concentrated hydrochloric acid. Acetone was added to precipitate the hydrochloride formed (1.8 g). The product was filtered off and recrystallized from 15 mL of ethanol to give 0.8 g of dihydrochlorided product with the following elemental analyses:

|   | THEORY, 2HCl | FOUND |
|---|---|---|
| C | 41.94 | 42.07 |
| H | 6.23 | 6.39 |
| N | 11.29 | 11.11 |

|   | THEORY, 2HCl | FOUND |
|---|---|---|
| Cl | 19.05 | 19.32 |
| S | 8.60 | 8.61 |

The proton NMR and mass spectra were in accordance with the expected structure of the product.

Example 3

Synthesis of 2-(4-aminophenylamino)ethanesulfonamide (13)

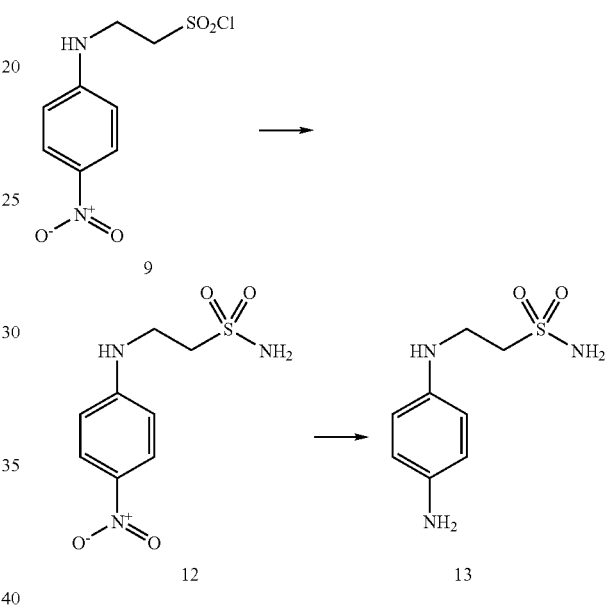

Step 1: Preparation of 2-(4-nitrophenylamino)ethanesulfonamide (12)

2-[(4-Nitrophenyl)amino]ethanesulfonyl chloride (9) (0.5 g) was mixed with 4 mL of aqueous ammonia (22%) at room temperature. The mixture was left for 1 hour and the precipitate that formed was then filtered off by suction and reslurried in water. The crude product was recrystallized from ethanol to give 0.23 g of expected product with a melting point of 170° C. The results of the elemental analysis were as follows:

|   | THEORY | FOUND |
|---|---|---|
| C | 39.17 | 38.61 |
| H | 4.52 | 4.86 |
| N | 17.13 | 16.12 |
| S | 13.07 | 12.91 |

Step 2: Preparation of 2-(4-aminophenylamino)ethanesulfonamide (13)

1 g of 2-(4-nitrophenylamino)ethanesulfonamide (12) was suspended in 10 mL of ethanol. At room temperature, the suspension was poured onto a reductive solution of sodium hydrosulfite (8 g)—1N sodium hydroxide (30 mL).

After decolorization, a precipitate formed. 0.7 g of crude product was isolated by suction-filtering and reslurrying in water.

The elemental analyses were as follows:

|   | THEORY | FOUND |
|---|--------|-------|
| C | 44.63  | 43.74 |
| H | 6.09   | 6.18  |
| N | 19.52  | 18.59 |
| S | 14.89  | 14.27 |

The proton NMR and mass spectra were in accordance with the expected structure of the product.

Example 4

Synthesis of 2-(4-aminophenylamino)ethanesulfonylmethylamide (15)

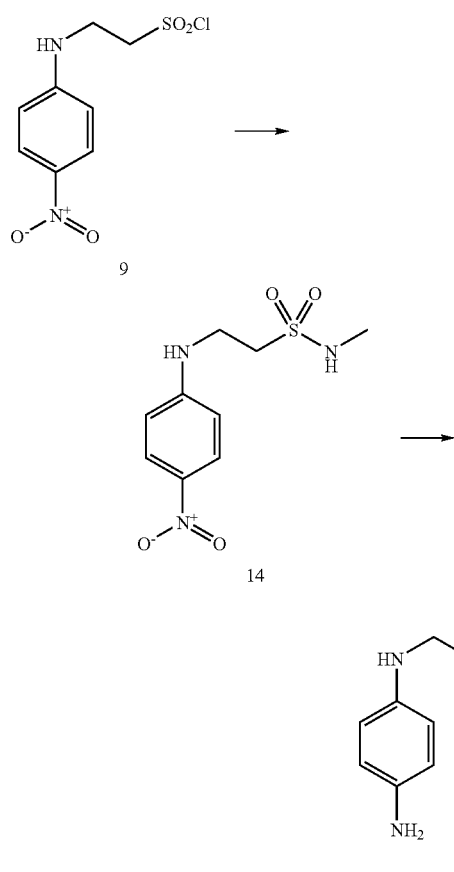

Step 1: Preparation of 2-(4-nitrophenylamino)ethanesulfonylmethylamide (14)

5 mL of monomethylamine (40% aqueous solution) were cooled in an ice bath and 2-[(4-nitrophenyl)amino]ethanesulfonyl (9) (2.6 g, 0.01 mol) was added in fractions. A yellow precipitate formed and the mixture was left overnight at room temperature. The product was filtered off by suction, reslurried in water, and dried. The crude product (2 g) was recrystallized from ethanol to give 1.57 g after drying. This product had a melting point of 130° C. and the following elemental analyses:

|   | THEORY | FOUND |
|---|--------|-------|
| C | 41.70  | 71.80 |
| H | 5.06   | 5.40  |
| N | 16.21  | 16.32 |
| S | 12.34  | 12.34 |

Step 2: Preparation of 2-(4-aminophenylamino)ethanesulfonylmethylamide (15)

A mixture of zinc powder (25 g), ammonium chloride (1.5 g), water (5 mL), and 96% ethanol (70 mL) was brought to reflux in a boiling water bath. The derivative 2-(4-nitrophenylamino)ethanesulfonylmethylamide (14) (13 g, 0.05 mol) was added in portions and heating was continued until the reaction medium decolorized. The resulting mixture was filtered while boiling and the filtrate was recovered onto 10 mL of concentrated hydrochloric acid. The zinc was washed with hot ethanol and the filtrate was left in a refrigerator for 1 day. 6.11 g of product with the following elemental analyses were isolated:

|    | THEORY, 2HCl | FOUND |
|----|--------------|-------|
| C  | 35.77        | 35.73 |
| H  | 5.67         | 5.85  |
| N  | 13.90        | 13.94 |
| Cl | 23.47        | 23.33 |

The proton NMR and mass spectra were in accordance with the expected structure of the product.

Example 5

Synthesis of 2-(4-aminophenylamino)ethanesulfonyl-2-hydroxyethylamide (17)

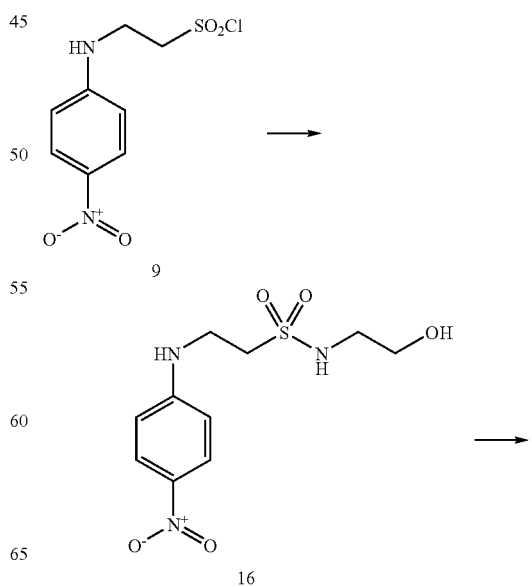

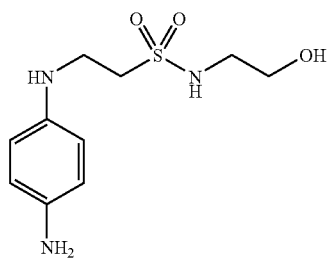

17

Step 1: Preparation of 2-(4-nitrophenylamino)ethanesulfonyl-(2-hydroxyethyl)amide (16)

30 g of ethanolamine were cooled in an ice bath and 13 g (0.05 mol) of 2-[(4-nitrophenyl)amino]ethanesulfonyl (9) were added in fractions. The mixture was left at room temperature for 40 hours and then poured into 200 mL of cold 2.5N hydrochloric acid. The resulting mixture was extracted with ethyl acetate and the organic phase was washed with hydrochloric acid and then with water. The ethyl acetate phase was dried and concentrated to 20 mL, and the product was then left to crystallize. After suction-filtering and drying, 7.73 g of expected product, with a melting point of 14° C., were isolated.

Step 2: Preparation of 2-(4-aminophenylamino)ethanesulfonyl-(2-hydroxyethyl)amide (17)

A mixture of zinc powder (5 g), ammonium chloride (0.3 g), water (1 mL), and 96% ethanol (14 mL) was refluxed in a boiling water bath. The derivative 2-(4-nitrophenylamino)ethanesulfonyl-(2-hydroxyethyl)amide (16) (2.89 g, 0.01 mol) was added in portions and heating was continued until the reaction medium had decolorized (30 minutes). The resulting mixture was filtered while boiling and the filtrate was recovered onto 2 ml of concentrated hydrochloric acid. The zinc was washed with 5 mL of ethanol, the filtrate was cooled on ice, and the precipitate that formed (m=1.88 g) was filtered off by suction. After recrystallization from 30 mL of ethanol, 1.5 g of expected compound having the following elemental analyses were isolated:

|   | THEORY, 1HCl | FOUND |
|---|---|---|
| C | 40.61 | 40.47 |
| H | 6.13 | 6.13 |
| N | 14.21 | 14.08 |
| Cl | 11.99 | 12.20 |
| S | 10.82 | 10.60 |

The proton NMR and mass spectra were in accordance with the expected structure of the product.

Example 6

Synthesis of 2-(4-aminophenylamino)ethanesulfonamide dihydrochloride (20)

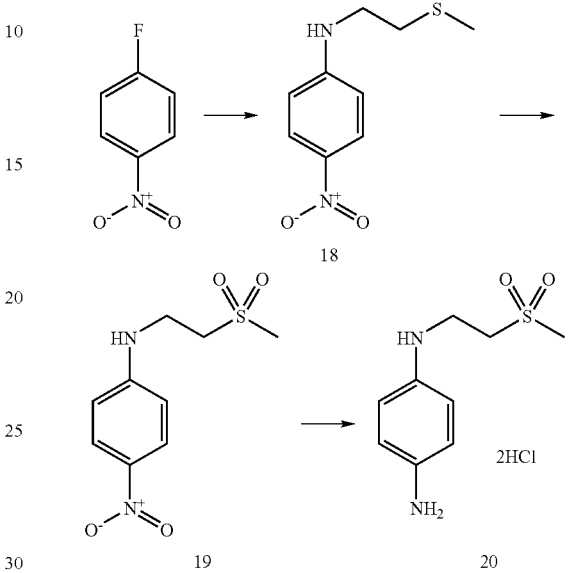

Step 1: Preparation of (2-methylsulfanylethyl)(4-nitrophenyl)amine (18)

2-aminoethanethiol dihydrochloride (45.4 g, 0.4 mol), water (100 mL), and 56.8 g (0.4 mol) of methyl iodide were mixed together. 16.5 g of sodium hydroxide pellets (0.4 mol) were dissolved in 100 mL of water and this solution was poured dropwise into the reaction mixture, while maintaining the temperature between 27-30° C. The resulting mixture was then stirred for 1 hour at 40° C. 21.2 g (10.2 mol) of para-fluoronitrobenzene and then 42 mL of triethylamine were added and the mixture was maintained in a boiling water bath for 3 hours. The resulting mixture was left overnight at room temperature and then acidified with hydrochloric acid and extracted with ethyl acetate. After evaporation to dryness, the 30 g of oil obtained were dissolved in 100 mL of 36% HCl. The resulting solution was extracted with ethyl ether to remove the starting material and, when cold, the aqueous phase was neutralized with aqueous ammonia. The resulting aqueous phase was extracted again with ethyl ether, dried, and evaporated to dryness to give 11 g of oil.

Purification by chromatography on silica allowed 20 g of pure expected product having the following elemental analyses to be isolated:

|   | THEORY | FOUND |
|---|---|---|
| C | 50.94 | 51.10 |
| H | 5.70 | 5.74 |
| N | 13.20 | 13.25 |
| O | 15.08 | 15.20 |
| S | 15.08 | 15.15 |

Step 2: Preparation of (2-methanesulfonylethyl)(4-nitrophenyl)amine (19)

8.4 g (0.04 mol) of (2-methylsulfanylethyl)(4-nitrophenyl)amine (18) were dissolved in 40 mL of acetic acid at room temperature. 18.7 mL (0.16 mol) of aqueous hydrogen peroxide solution (30% solution) were added dropwise while maintaining the temperature at 40-45° C. with an ice bath. The mixture was gradually heated in a boiling water bath, up to 95° C. It was left for 45 minutes and was then poured onto 80 mL of ice-water. The brown crystals that formed were filtered off by suction, dried, and then recrystallized from 120 mL of 96% ethanol. 4.6 g of product were isolated and then taken up in 50 mL of concentrated hydrochloric acid and 5 mL of water. The insoluble matter was filtered off and the filtrate was neutralized, while cooling, with aqueous ammonia. The orange-brown crystals were filtered off by suction and dried over $P_2O_5$. The resulting product weighed 3.2 g and had a melting point of 149° C. The product was recrystallized from 120 ml of ethyl acetate to give 2.3 g of yellow crystals with a melting point of 150° C., which had the following elemental analyses:

|   | THEORY | FOUND |
|---|--------|-------|
| C | 44.26  | 44.29 |
| H | 4.95   | 4.97  |
| N | 11.47  | 11.45 |
| O | 26.20  | 26.00 |
| S | 13.11  | 13.05 |

Step 3: Preparation of N-(2-methanesulfonylethyl)benzene-1,4-diamine dihydrochloride (20)

1.8 g (7.37 mmol) of (2-methanesulfonylethyl)(4-nitrophenyl)amine (19) were dissolved in 70 mL of absolute ethanol. The solution was hydrogenated for 90 minutes under 60 bar of hydrogen at 50° C. in the presence of 1.5 g of 10% palladium-on-charcoal. The catalyst was filtered off and the filtrate was recovered onto 5 mL of 6.4N hydrochloric ethanol. The resulting mixture was cooled and the product was filtered off by suction and dried over $P_2O_5$/KOH to give 1.4 g of white crystals.

The proton NMR and mass spectra were in accordance with the expected structure of the product.

Example 7

Synthesis of N-[2-(4-aminophenylamino)ethyl]-N-methylmethanesulfonamide sulfate (24)

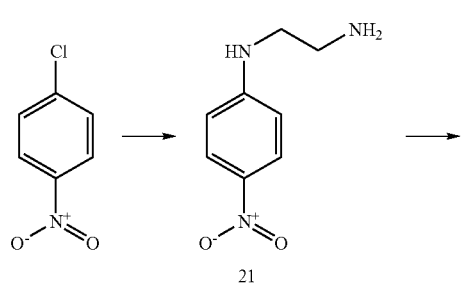

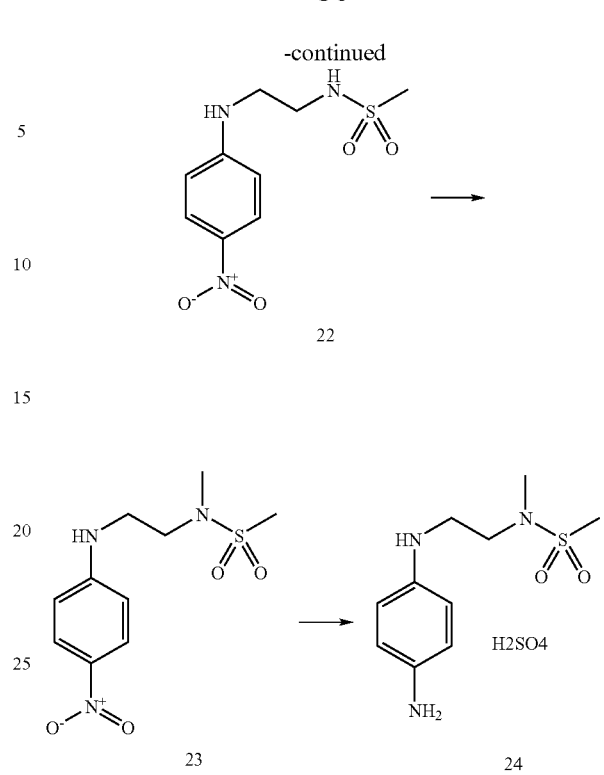

Step 1: Preparation of N-1-(4-nitrophenyl)ethane-1,2-diamine (21)

1382 g (23 mol) of ethylenediamine were heated in a boiling water bath. A solution of para-chloronitrobenzene (906 g, 5.75 mol in 900 g of pyridine) was then added over 15 minutes, and heating was continued for 2 hours. When the reaction was complete, the medium was poured onto 15 kg of ice-water. The yellow precipitate that formed was filtered off by suction and reslurried three times in water. The crude product obtained was dissolved in 6 L of 2N hydrochloric acid and stirred for 1 hour, and the hydrochloride was then filtered off. The product obtained was dissolved in 12 L of boiling water. The traces of residue were filtered off while hot and the filtrate was cooled to 80° C., and then basified with aqueous ammonia to pH=12. A yellow precipitate formed and was filtered off when cold. It was then washed and recrystallized from 3 L of 96% ethanol. After drying under vacuum, 716 g of expected product with a melting point of 150° C. were obtained.

Step 2: Preparation of N-[2-(4-nitrophenylamino)ethyl]methanesulfonamide (22)

90.5 g (0.5 mol) of N-1-(4-nitrophenyl)ethane-1,2-diamine (21) were suspended in 400 mL of pyridine. The mixture was heated to 45° C. and 63 g (0.55 mol) of mesyl chloride were added, while maintaining the temperature ranging from 45 to 50° C. The solution obtained was stirred for 1 hour at 50° C. It was then poured onto 2 kg of ice and 300 mL of concentrated hydrochloric acid with stirring. The yellow precipitate was filtered off by suction and reslurried three times in water, and dried. 129 g of yellow powder with a melting point of 154° C. were obtained in quantitative yield.

Step 3: Preparation of N-methyl-N-[2-(4-nitrophenylamino) ethyl]methanesulfonamide (23)

25.9 g (0.1 mol) of N-[2-(4-nitrophenylamino)ethyl] methanesulfonamide (22) were dissolved in 200 mL of 1N sodium hydroxide at 50° C. The insoluble matter was filtered off, the filtrate was cooled to 30° C. and 11.4 mL (0.12 mol) of methyl sulfate were added dropwise. The mixture was stirred for 1 hour at room temperature and then heated to 40° C. and the yellow precipitate was filtered off. The product was reslurried in 0.5N sodium hydroxide and in water. The wet crude product was recrystallized from 50 mL of 96% ethanol with carbon black. 13.3 g of product with a melting point of 109° C. were isolated.

|   | THEORY | FOUND |
|---|---|---|
| C | 43.95 | 44.12 |
| H | 5.53 | 5.76 |
| N | 15.38 | 15.13 |
| O | 11.77 | 11.98 |

The proton NMR and mass spectra were in accordance with the expected structure of the product.

Step 4: Preparation of N-[2-(4-aminophenylamino)ethyl]-N-methylmethanesulfonamide sulfate (24)

A mixture of zinc powder (25 g), ammonium chloride (1.1 g), water (11.2 mL), and 96% ethanol (67.5 mL) was brought to reflux in a boiling water bath. N-methyl-N-[2-(4-nitrophenylamino)ethyl]methanesulfonamide (23) (12.3 g, 0.045 mol) was added in portions and heating was continued until the reaction medium decolorized. The resulting mixture was filtered while boiling and the filtrate was recovered onto 3.8 mL of 96% sulfuric acid. The zinc was washed with ethanol, the filtrate was cooled in ice, and the precipitate that formed was filtered off by suction. After recrystallization from 30 mL of ethanol and 30 mL of water, 14.4 g of product were isolated. A second recrystallization from 45 mL of 50% ethanol gave 11.5 g of expected product having the following elemental analyses:

|   | THEORY, $H_2SO_4$ | FOUND |
|---|---|---|
| C | 35.18 | 35.40 |
| H | 5.61 | 5.88 |
| N | 12.31 | 12.37 |
| O | 18.78 | 18.71 |

The proton NMR and mass spectra were in accordance with the expected structure of the product.

Example 8

Synthesis of N-[4-(4-aminophenylamino)butyl]methanesulfonamide sulfate (27)

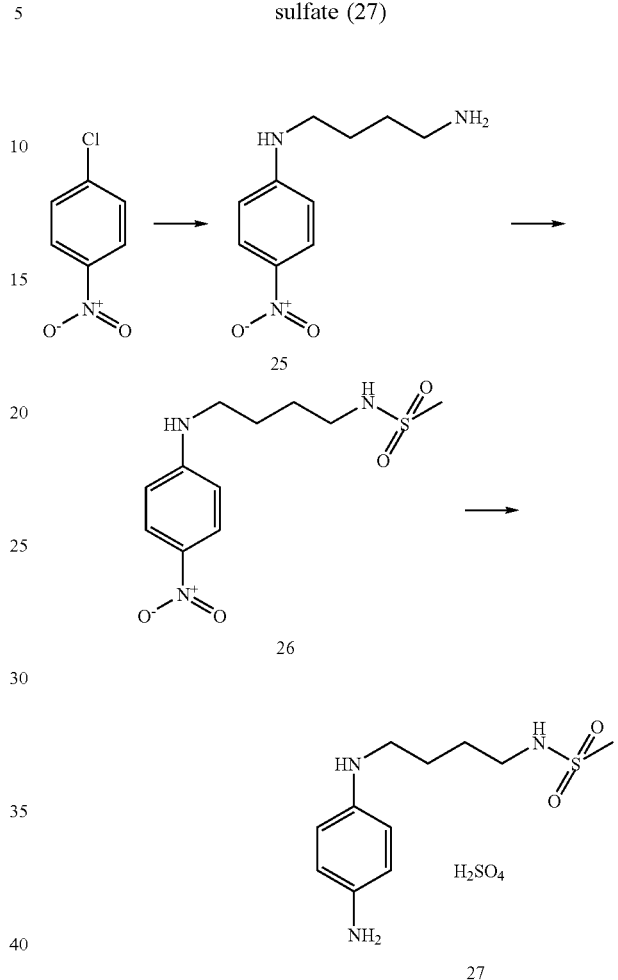

Step 1: Preparation of N-1-(4-nitrophenyl)butane-1,4-diamine (25)

A solution of 78.75 g (0.5 mol) of 4-chloronitrobenzene was added over 15 minutes to 176.3 g (2 mol) of 1,4-diaminobutane heated in a boiling water bath. After stirring for 4 hours, the reaction mixture was poured onto 1 kg of ice-water. The precipitate was filtered off by suction, washed with water, and then dried. The weight obtained after recrystallization from 200 mL of acetonitrile was 86.7 g. The melting point was 103° C.

Step 2: Preparation of N-[4-(4-nitrophenylamino)butyl] methanesulfonamide (26)

The N-1-(4-nitrophenyl)butane-1,4-diamine (25) obtained in the preceding step (86.5 g, 0.409 mol) was dissolved in 340 mL of pyridine at 40° C. 35.1 mL (0.45 mol) of mesyl chloride were then added dropwise so as to maintain the temperature at about 50° C. After stirring for 1 hour, the solution was poured onto 820 g of ice and 285 ml of concentrated hydrochloric acid. The yellow precipitate that formed was filtered off by suction, washed with hydrochloric acid, and then with water, and was then dried.

The weight of the product obtained after recrystallization from acetonitrile was 90.6 g. The melting point was 153° C.

Step 3: Preparation of N-[4-(4-aminophenylamino)butyl]methanesulfonamide sulfate (27)

25.6 g (0.0891 mol) of N-[4-(4-nitrophenylamino)butyl]methanesulfonamide (26) were hydrogenated in a mixture of 49 g of zinc powder, 1.6 g of ammonium chloride, 24 mL of water, and 135 mL of ethanol brought to reflux. After suction-filtering of the slurry, the para-phenylenediamine was isolated in the form of a sulfate by addition of 8.1 mL of 96% sulfuric acid. After filtration and drying, 31.3 g of grey product were obtained.

The proton NMR and mass spectra were in accordance with the expected structure of the product.

Example 9

Synthesis of 2-(4-aminophenylamino)-4-methylsulfanylbutyric acid methyl ester (29)

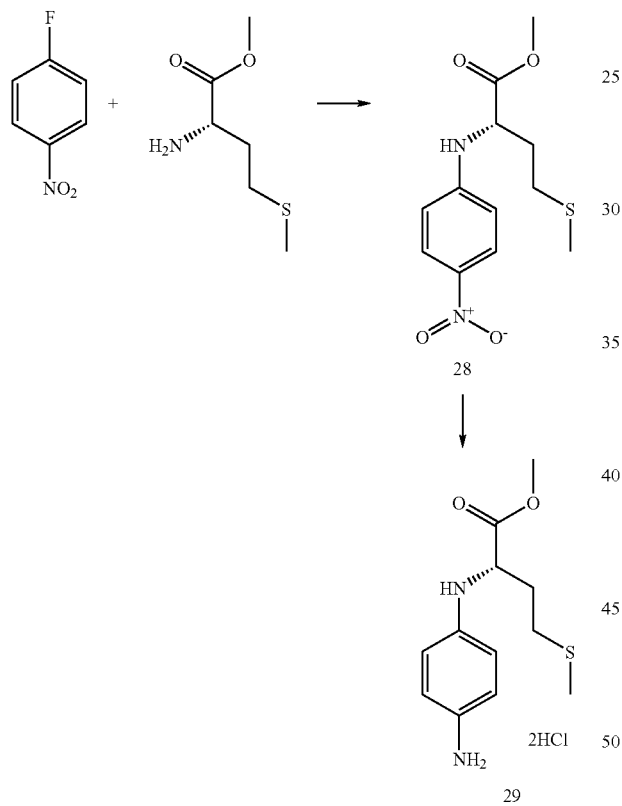

Step 1: Synthesis of 4-methylsulfanyl-2-(4-nitrophenylamino)butyric acid methyl ester (28)

1 g of 4-fluoro-3-methylnitrobenzene, 0.694 g of L-methionine methyl ester and 1.09 ml of triethylamine were added to a solution of 5 ml of N-methylpyrrolidinone. The reaction medium was heated at 90° C. for 7 hours and, after cooling to room temperature, was poured into an ice water mixture. The reaction medium was then extracted with ethyl acetate and the organic phase was dried and concentrated to dryness. After purification by chromatography on a column of silica, 4-methylsulfanyl-2-(4-nitrophenylamino)butyric acid methyl ester (28) was obtained.

Step 2: Synthesis of 2-(4-aminophenylamino)-4-methylsulfanylbutyric acid methyl ester dihydrochloride (29)

The 4-methylsulfanyl-2-(4-nitrophenylamino)butyric acid methyl ester (28) obtained above was reduced with a boiling zinc/ammonium chloride/water/ethanol mixture. The corresponding amine was isolated in dihydrochloride form.

The proton NMR and mass spectra were in accordance with the expected structure of the product.

DYEING EXAMPLES

Dyeing Examples 1 to 11

Dye Composition from N-{2-[(4-aminophenyl)amino]ethyl}benzenesulfonamide (3)

Examples 1 to 6

Dyeing in Acidic Medium

The following dye compositions were prepared:

|  | Example |  |  |  |  |  |
| --- | --- | --- | --- | --- | --- | --- |
|  | 1 | 2 | 3 | 4 | 5 | 6 |
| N-{2-[(4-Aminophenyl)-amino]ethyl}benzenesulfonamide(3) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol |  |  |  |  |  |
| 5-Amino-2-methylphenol |  | $10^{-3}$ mol |  |  |  |  |
| 1H-Indol-6-ol |  |  | $10^{-3}$ mol |  |  |  |

-continued

|  | Example | | | | | |
|---|---|---|---|---|---|---|
|  | 1 | 2 | 3 | 4 | 5 | 6 |
| 2-Aminopyridin-3-ol |  |  |  | $10^{-3}$ mol |  |  |
| 3,6-Dimethyl-1H-pyrazolo[5,1-c]-[1,2,4]triazole |  |  |  |  | $10^{-3}$ mol |  |
| 2-(2,4-Diaminophenoxy)-ethanol hydrochloride |  |  |  |  |  | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | |
|---|---|---|---|---|---|---|
|  | 1 | 2 | 3 | 4 | 5 | 6 |
| Shade observed | yellow-brown | red-violet | strong red-brown | strong red-brown | red | strong blue |

Examples 7 to 11

Dyeing in Basic Medium

The following dye compositions were prepared:

|  | Example | | | | |
|---|---|---|---|---|---|
|  | 7 | 8 | 9 | 10 | 11 |
| N-{2-[(4-Aminophenyl)-amino]ethyl}benzene-sulfonamide(3) | $10^{-3}$ mol | $10^{-3}$ mol | $10^{-3}$ mol | $10^{-3}$ mol | $10^{-3}$ mol |
| 5-Amino-2-methyl-phenol | $10^{-3}$ mol |  |  |  |  |
| 1H-Indol-6-ol |  | $10^{-3}$ mol |  |  |  |
| 2-Aminopyridin-3-ol |  |  | $10^{-3}$ mol |  |  |
| 3,6-Dimethyl-1H-pyrazolo[5,1-c]-[1,2,4]triazole |  |  |  | $10^{-3}$ mol |  |
| 2-(2,4-Diaminophenoxy)-ethanol hydrochloride |  |  |  |  | $10^{-3}$ mol |
| Dye support (2) | (*) | (*) | (*) | (*) | (*) |

-continued

| | Example | | | | |
|---|---|---|---|---|---|
| | 7 | 8 | 9 | 10 | 11 |
| Demineralized water qs | 100 g | 100 g | 100 g | 100 g | 100 g |

(*): dye support (2) pH 9.5

| 96° ethyl alcohol | 20.8 g |
|---|---|
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

The shades obtained are given in the table below:

| | Example | | | | |
|---|---|---|---|---|---|
| | 7 | 8 | 9 | 10 | 11 |
| Shade observed | red | orange | red | chromatic red | strong blue |

Dyeing Examples 12 to 24
Dye Composition from 2-[(4-aminophenyl)amino]-N-(tetrahydrofuran-2-ylmethyl)ethanesulfonamide dihydrochloride (11)

Examples 12 to 18
Dyeing in Acidic Medium
The following dye compositions were prepared:

| | Example | | | | | | |
|---|---|---|---|---|---|---|---|
| | 12 | 13 | 14 | 15 | 16 | 17 | 18 |
| 2-[(4-Aminophenyl)amino]-N-(tetrahydrofuran-2-ylmethyl)-ethanesulfonamide dihydrochloride (11) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methyl-phenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

| 96° ethyl alcohol | 20.8 g |
|---|---|
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |

-continued

| | |
|---|---|
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

| | Example | | | | | |
|---|---|---|---|---|---|---|
| | 12 | 13 | 14 | 15 | 16 | 17 | 18 |
| Shade observed | strong brown | strong red-violet | strong red-brown | strong red-brown | strong red-grey | strong blue | strong violet |

-continued

| | |
|---|---|
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

Examples 19 to 24

Dyeing in Basic Medium

The following dye compositions were prepared:

| | Example | | | | | |
|---|---|---|---|---|---|---|
| | 19 | 20 | 21 | 22 | 23 | 24 |
| 2-[(4-Aminophenyl)amino]-N-(tetrahydrofuran-2-yl-methyl)ethanesulfonamide dihydrochloride (11) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo-[5,1-c][1,2,4]triazole | | | | $10^{-3}$ mol | | |
| 2-(2,4-Diaminophenoxy)-ethanol hydrochloride | | | | | $10^{-3}$ mol | |
| 3-Amino-2-chloro-6-methylphenol hydrochloride | | | | | | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |

The shades obtained are given in the table below:

| | Example | | | | | |
|---|---|---|---|---|---|---|
| | 19 | 20 | 21 | 22 | 23 | 24 |
| Shade observed | red | orange | red | chromatic red | strong blue | strong violet |

Dyeing Examples 25 to 29

Dye Composition from 2-(4-Aminophenylamino)ethanesulfonamide (13)

Examples 25 to 28

Dyeing in Acidic Medium

The following dye compositions were prepared:

|  | Example | | | |
| --- | --- | --- | --- | --- |
|  | 25 | 26 | 27 | 28 |
| 2-(4-Aminophenylamino)ethanesulfonamide (13) | $10^{-3}$ mol | $10^{-3}$ mol | $10^{-3}$ mol | $10^{-3}$ mol |
| 5-Amino-2-methylphenol | $10^{-3}$ mol | | | |
| 1H-Indol-6-ol | | $10^{-3}$ mol | | |
| 2-Aminopyridin-3-ol | | | $10^{-3}$ mol | |
| 2-(2,4-Diaminophenoxy)-ethanol hydrochloride | | | | $10^{-3}$ mol |
| Dye support (1) | (*) | (*) | (*) | (*) |
| Demineralized water qs | 100 g | 100 g | 100 g | 100 g |

(*): dye support (1) pH 7

| | |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | |
| --- | --- | --- | --- | --- |
|  | 25 | 26 | 27 | 28 |
| Shade observed | red | orange-brown | red-brown | strong blue-grey |

Example 29
Dyeing in Basic Medium

The dye composition below was prepared:

|  | Example 29 |
| --- | --- |
| 2-(4-Aminophenylamino)-ethanesulfonamide (13) | $10^{-3}$ mol |

-continued

|  | Example 29 |
| --- | --- |
| 2-(2,4-Diaminophenoxy)-ethanol hydrochloride | $10^{-3}$ mol |
| Dye support (2) | (*) |
| Demineralized water qs | 100 g |

(*): dye support (2) pH 9.5

| | |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, the composition was mixed with an equal weight of 20-volumes aqueous hydrogen peroxide solution (6% by weight). A final pH of 9.5 was obtained.

The mixture obtained was applied to locks of grey hair containing 90% white hairs. 30 minutes after application, the locks were rinsed, washed with a standard shampoo, rinsed again, and then dried.

The shade obtained is given in the table below:

|  | Example 29 |
|---|---|
| Shade observed | blue-grey |

Dyeing Examples 30 to 40

Dye Composition from 2-(4-Aminophenylamino)ethanesulfonyl methylamide (15)

Examples 30 to 35

Dyeing in Acidic Medium

The following dye compositions were prepared:

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | |
|---|---|---|---|---|---|---|
|  | 30 | 31 | 32 | 33 | 34 | 35 |
| Shade observed | strong brown | strong red-violet | strong red-brown | strong red | strong red-brown | strong blue-violet |

|  | Example | | | | | |
|---|---|---|---|---|---|---|
|  | 30 | 31 | 32 | 33 | 34 | 35 |
| 2-(4-Aminophenylamino) ethanesulfonyl methylamide (15) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | |
| 5-Amino-2-methylphenol | | $10^{-3}$ mol | | | | |
| 1H-Indol-6-ol | | | $10^{-3}$ mol | | | |
| 2-Aminopyridin-3-ol | | | | $10^{-3}$ mol | | |
| 3,6-Dimethyl-1H-pyrazolo-[5,1-c][1,2,4]triazole | | | | | $10^{-3}$ mol | |
| 2-(2,4-Diaminophenoxy)-ethanol hydrochloride | | | | | | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

Examples 36 to 40

Dyeing in Basic Medium

The following dye compositions were prepared:

|  | Example | | | | |
| --- | --- | --- | --- | --- | --- |
|  | 36 | 37 | 38 | 39 | 40 |
| 2-(4-Aminophenylamino)-ethanesulfonyl methylamide (15) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 3,6-Dimethyl-1H-pyrazolo-[5,1-c][1,2,4]triazole | | | | $10^{-3}$ mol | |
| 2-(2,4-Diaminophenoxy)-ethanol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

(*): dye support (2) pH 9.5

| | |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | |
| --- | --- | --- | --- | --- | --- |
|  | 36 | 37 | 38 | 39 | 40 |
| Shade observed | red | orange | red | chromatic red | strong blue |

Dyeing Examples 41 to 51

Dye Composition from 2-(4-aminophenylamino) ethanesulfonyl(2-hydroxyethyl)amide (17)

Examples 41 to 47

Dyeing in Acidic Medium

The following dye compositions were prepared:

|  | Example | | | | | | |
| --- | --- | --- | --- | --- | --- | --- | --- |
|  | 41 | 42 | 43 | 44 | 45 | 46 | 47 |
| 2-(4-Aminophenylamino)-ethanesulfonic acid (2-hydroxyethyl)amide (17) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4- | | | | | | $10^{-3}$ mol | |

-continued

|  | Example | | | | | | |
|---|---|---|---|---|---|---|---|
|  | 41 | 42 | 43 | 44 | 45 | 46 | 47 |
| Diaminophenoxy)-ethanol hydrochloride |  |  |  |  |  |  |  |
| 3-Amino-2-chloro-6-methyl-phenol hydrochloride |  |  |  |  |  |  | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | | |
|---|---|---|---|---|---|---|---|
|  | 41 | 42 | 43 | 44 | 45 | 46 | 47 |
| Shade observed | orange-brown | red | red-brown | red | orange-brown | strong blue-grey | strong violet |

Examples 48 to 51

Dyeing in Basic Medium

The following dye compositions were prepared:

|  | Example | | | |
|---|---|---|---|---|
|  | 48 | 49 | 50 | 51 |
| 2-(4-Aminophenylamino)-ethanesulfonic acid (2-hydroxyethyl)amide | $10^{-3}$ mol | $10^{-3}$ mol | $10^{-3}$ mol | $10^{-3}$ mol |
| (17) 1H-Indol-6-ol | $10^{-3}$ mol |  |  |  |
| 3,6-Dimethyl-1H-pyrazolo-[5,1-c][1,2,4]triazole |  | $10^{-3}$ mol |  |  |
| 2-(2,4-Diaminophenoxy)-ethanol hydrochloride |  |  | $10^{-3}$ mol |  |
| 3-Amino-2-chloro-6-meth-ylphenol hydrochloride |  |  |  | $10^{-3}$ mol |
| Dye support (2) | (*) | (*) | (*) | (*) |
| Demineralized water qs | 100 g | 100 g | 100 g | 100 g |

(*): dye support (2) pH 9.5

| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | |
|---|---|---|---|---|
|  | 48 | 49 | 50 | 51 |
| Shade observed | orange | red | blue | violet |

Dyeing Examples 52 to 65

Dye Composition from N-[2-(4-Aminophenyl-amino)ethyl]-N-methylmethanesulfonamide sulfate (24)

Examples 52 to 58

Dyeing in Acidic Medium

The following dye compositions were prepared:

|  | Example | | | | | | |
|---|---|---|---|---|---|---|---|
|  | 52 | 53 | 54 | 55 | 56 | 57 | 58 |
| N-[2-(4-Aminophenylamino)ethyl]-N-methylmethanesulfonamide sulfate (24) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | | |
|---|---|---|---|---|---|---|---|
|  | 52 | 53 | 54 | 55 | 56 | 57 | 58 |
| Shade observed | strong grey | strong violet-grey | strong red-brown | strong red-brown | strong grey | strong blue | strong violet |

Examples 59 to 65

Dyeing in Basic Medium

The following dye compositions were prepared:

| | Example | | | | | | |
|---|---|---|---|---|---|---|---|
| | 59 | 60 | 61 | 62 | 63 | 64 | 65 |
| N-[2-(4-Aminophenylamino)ethyl]-N-methyl-methanesulfonamide, sulfate (24) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-meth-ylphenol hydrochloride | | | | | | | $10^{-3}$ mol |
| Dye support (2) | (*) | (*) | (*) | (*) | (*) | (*) | (*) |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

| | Example | | | | | | |
|---|---|---|---|---|---|---|---|
| | 59 | 60 | 61 | 62 | 63 | 64 | 65 |
| Shade observed | yellow | red-violet | red | red | chromatic red | strong blue | strong violet |

Dyeing Examples 66 to 77

Dye Composition from N-[4-(4-Aminophenylamino)butyl]methanesulfonamide (27)

Examples 66 to 71

Dyeing in Acidic Medium

The following dye compositions were prepared:

| | Example | | | | | |
|---|---|---|---|---|---|---|
| | 66 | 67 | 68 | 69 | 70 | 71 |
| N-[4-(4-Aminophenylamino)-butyl]methanesulfonamide sulfate (27) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | |
| 5-Amino-2-methylphenol | | $10^{-3}$ mol | | | | |
| 1H-Indol-6-ol | | | $10^{-3}$ mol | | | |
| 2-Aminopyridin-3-ol | | | | $10^{-3}$ mol | | |

|  | Example | | | | | |
| --- | --- | --- | --- | --- | --- | --- |
|  | 66 | 67 | 68 | 69 | 70 | 71 |
| 3,6-Dimethyl-1H-pyrazolo-[5,1-c][1,2,4]triazole |  |  |  |  | $10^{-3}$ mol |  |
| 2-(2,4-Diaminophenoxy)ethanol hydrochloride |  |  |  |  |  | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

| 96° ethyl alcohol | 20.8 g |
| --- | --- |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | |
| --- | --- | --- | --- | --- | --- | --- |
|  | 66 | 67 | 68 | 69 | 70 | 71 |
| Shade observed | strong brown | strong violet | strong red-grey | strong red-violet | strong red-grey | strong blue violet grey |

Examples 72 to 77
Dyeing in Basic Medium

The following dye compositions were prepared:

|  | Example | | | | | |
| --- | --- | --- | --- | --- | --- | --- |
|  | 72 | 73 | 74 | 75 | 76 | 77 |
| N-[4-(4-Aminophenylamino)butyl]methanesulfonamide sulfate (27) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol |  |  |  |  |  |
| 5-Amino-2-methylphenol |  | $10^{-3}$ mol |  |  |  |  |
| 1H-Indol-6-ol |  |  | $10^{-3}$ mol |  |  |  |
| 2-Aminopyridin-3-ol |  |  |  | $10^{-3}$ mol |  |  |
| 3,6-Dimethyl-1H-pyrazolo-[5,1-c][1,2,4]triazole |  |  |  |  | $10^{-3}$ mol |  |
| 2-(2,4-Diaminophenoxy)-ethanol hydrochloride |  |  |  |  |  | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*): dye support (2) pH 9.5

| 96° ethyl alcohol | 20.8 g |
| --- | --- |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | | |
|---|---|---|---|---|---|---|
|  | 72 | 73 | 74 | 75 | 76 | 77 |
| Shade observed | yellow | strong violet | red | red-brown | strong red | strong blue |

Dyeing Examples 78 to 84

Dye Composition Using 2-(4-aminophenylamino)-4-methyl-sulfanylbutyric acid methyl ester dihydrochloride (29)

Examples 78 to 82

Dyeing in Acid Medium

The following dye compositions were prepared:

|  | Example | | | | |
|---|---|---|---|---|---|
|  | 78 | 79 | 80 | 81 | 82 |
| 2-(4-Aminophenylamino)-4-methylsulfanylbutyric acid methyl ester dihydrochloride (29) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| Na$_2$HPO$_4$ | 0.28 g |
| KH$_2$PO$_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | | | | |
|---|---|---|---|---|---|
|  | 78 | 79 | 80 | 81 | 82 |
| Shade observed | red | brown | red | strong grey | red |

Examples 83 and 84

Dyeing in Basic Medium

The following dye compositions were prepared:

|  | Example | |
|---|---|---|
|  | 83 | 84 |
| 2-(4-Aminophenylamino)-4-methylsulfanylbutyric acid methyl ester dihydrochloride (29) | $10^{-3}$ mol | $10^{-3}$ mol |

-continued

|  | Example | |
|---|---|---|
|  | 83 | 84 |
| 2-(2,4-Diaminophenoxy)-ethanol hydrochloride | $10^{-3}$ mol | |
| 3-Amino-2-chloro-6-methylphenol hydrochloride | | $10^{-3}$ mol |
| Dye support (2) | (*) | (*) |
| Demineralized water qs | 100 g | 100 g |

(*) dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again, and then dried.

The shades obtained are given in the table below:

|  | Example | |
| --- | --- | --- |
|  | 83 | 84 |
| Shade observed | blue-violet grey | red |

What is claimed is:

1. A sulfur-containing secondary para-phenylene diamine chosen from compounds of formula (I) and the addition salts thereof:

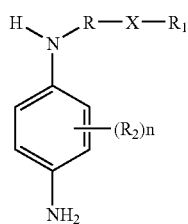

wherein:
- X is chosen from $SO_2$ and sulfur;
- if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
- if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
- $R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;
- $R_2$ is chosen from hydrogen, halogen atoms, and radicals chosen from alkyl, alkoxy, alkoxyalkyl, hydroxyalkoxy, monohydroxyalkyl, and polyhydroxyalkyl; and
- n is an integer ranging from 1 to 4;

with the proviso that the compound of formula (I) is not:
- 2-(4-Amino-3-methylphenylamino)ethanesulfonamide,
- 2-(4-Aminophenylamino)ethanesulfonic acid diethylamide,
- N-[2-(4-Amino-2-methylphenylamino)ethyl]methanesulfonamide,
- N-[2-(4-Aminophenylamino)ethyl]methanesulfonamide,
- 2-[3-(4-Aminophenylamino)propane-1-sulfonyl]ethanol,
- N-[3-(Butane-1-sulfonyl)propyl]benzene-1,4-diamine,
- N-[2-(4-Amino-3-methylphenylamino)ethyl]methanesulfonamide,
- N-[2-(4-Amino-2-methylphenylamino)ethyl]-N-ethylmethanesulfonamide
- [2-(4-Amino-3-methylphenylamino)ethyl]sulfamic acid,
- N-[2-(4-Amino-2-chlorophenylamino)ethyl]methanesulfonamide, or
- N-[3-(4-Aminophenylamino)propyl-3-oxo]benzenesulfonamide.

2. The sulfur-containing secondary para-phenylene diamine according to claim 1, wherein R is chosen from linear and branched $C_2$-$C_5$ alkylene radicals, which may be substituted with a radical chosen from —OH, —$COOCH_3$, and —$COOCH_2CH_3$, wherein at least one carbon atom of the alkylene radical is optionally replaced with at least one heteroatom chosen from oxygen, nitrogen, and sulfur atoms.

3. The sulfur-containing secondary para-phenylene diamine according to claim 1, wherein $R_1$ is chosen from alkyl, aryl, arylalkyl, and hydroxyalkyl groups, and secondary and tertiary amine groups.

4. The sulfur-containing secondary para-phenylene diamine according to claim 1, wherein $R_2$ is chosen from hydrogen and methyl.

5. The sulfur-containing secondary para-phenylene diamine according to claim 1, wherein the compound of formula (I) is chosen from:
- N-[2-(4-aminophenylamino)ethyl]benzenesulfonamide,
- 2-(4-Aminophenylamino)ethanesulfonic acid (tetrahydrofuran-2-ylmethyl)amide,
- 2-(4-Aminophenylamino)ethanesulfonic acid methylamide,
- 2-(4-Aminophenylamino)ethanesulfonic acid (2-hydroxyethyl)amide,
- 2-(4-Aminophenylamino)ethanesulfonic acid amide,
- N-[2-(4-Aminophenylamino)ethyl]-N-methylmethanesulfonamide,
- N-[4-(4-Aminophenylamino)butyl]methanesulfonamide,
- 2-(4-Aminophenylamino)ethanesulfonic acid bis(2-hydroxyethyl)amide,
- N-(2-Methanesulfonylethyl)benzene-1,4-diamine,
- Methanethiosulfonic acid S-[2-(4-aminophenylamino) ethyl]ester,
- 2-(4-Aminophenylamino)-4-methylsulfanyl butyric acid methyl ester,
- 2-(4-Aminophenylamino)-3-benzylsulfanylpropan-1-ol,
- 2-(4-Aminophenylamino)-3-benzylsulfanylpropionic acid ethyl ester,
- 2-(4-Aminophenylamino)-3-benzylsulfanylpropionic acid methyl ester, 2-(4-Aminophenylamino)-4-methylsulfanyl butyric acid ethyl ester,
N-[2-(4-Amino-2-methyl phenylamino)ethyl]benzenesulfonamide,
2-(4-Amino-2-methylphenylamino)ethanesulfonic acid (tetrahydrofuran-2-ylmethyl)amide,
2-(4-Amino-2-methylphenylamino)ethanesulfonic acid methylamide,
2-(4-Amino-2-methylphenylamino)ethanesulfonic acid (2-hydroxyethyl)amide,
2-(4-Amino-2-methylphenylamino)ethanesulfonic acid diethylamide,
2-(4-Amino-2-methylphenylamino)ethanesulfonic acid amide,
N-[2-(4-Amino-2-methylphenylamino)ethyl]-N-methyl-methanesulfonamide,
N[4-(4-Amino-2-methylphenylamino)butyl]methanesulfonamide,
2-(4-Amino-2-methylphenylamino)ethanesulfonic acid bis(2-hydroxyethyl)amide,
N-1-(2-Methanesulfonyl-ethyl)-2-methylbenzene-1,4-diamine,
Methanethiosulfonic acid S-[2-(4-amino-2-methylphenylamino)ethyl]ester,
2-(4-Amino-2-methylphenylamino)-4-methylsulfanylbutyric acid methyl ester,
2-(4-Amino-2-methylphenylamino)-3-benzylsulfanylpropan-1-ol,
2-(4-Amino-2-methylphenylamino)-3-benzylsulfanyl-propionic acid ethyl ester,
2-(4-Amino-2-methylphenylamino)-3-benzylsulfanylpropionic acid methyl ester,
N-[2-(4-Amino-3-methylphenylamino)ethyl]benzenesulfonamide,
2-(4-Amino-3-methyl phenylamino)ethanesulfonic acid (tetrahydrofuran-2-ylmethyl)amide,
2-(4-Amino-3-methylphenylamino)ethanesulfonic acid methylamide,
2-(4-Amino-3-methylphenylamino)ethanesulfonic acid (2-hydroxyethyl)amide,
2-(4-Amino-3-methylphenylamino)-4-methylsulfanyl butyric acid ethyl ester,
2-(4-Amino-3-methylphenylamino)ethanesulfonic acid diethylamide,
2-(4-Amino-2-methylphenylamino)-4-methylsulfanylbutyric acid ethyl ester,
N-[2-(4-Amino-3-methylphenylamino)ethyl]-N-methyl-methanesulfonamide,
N-[4-(4-Amino-3-methylphenylamino)butyl]methanesulfonamide,
2-(4-Amino-3-methylphenylamino)ethanesulfonic acid bis(2-hydroxyethyl)amide,
N-4-(2-Methanesulfonylethyl)-2-methylbenzene-1,4-diamine,
Methanethiosulfonic acid S-[2-(4-amino-3-methylphenylamino)ethyl]ester,
2-(4-Amino-3-methylphenylamino)-4-methylsulfanylbutyric acid methyl ester,
2-(4-Amino-3-methylphenylamino)-3-benzylsulfanylpropan-1-ol,
2-(4-Amino-3-methylphenylamino)-3-benzylsulfanyl-propionic acid ethyl ester,
2-(4-Amino-3-methylphenylamino)-3-benzylsulfanyl propionic acid methyl ester, and the addition salts thereof.

6. The sulfur-containing secondary para-phenylene diamine according to claim 1, wherein the addition salts of the compounds of formula (I) are acid addition salts chosen from hydrochlorides, hydrobromides, sulfates, citrates, succinates, tartrates, lactates, tosylates, benzenesulfonates, phosphates, and acetates.

7. A nitro compound, chosen from compounds of formula (II):

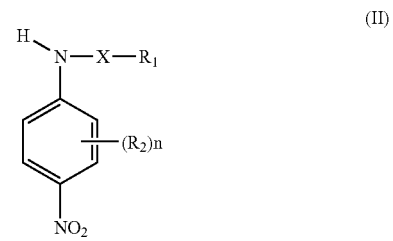

wherein:

x is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4.

8. A process for preparing sulfur-containing secondary para-phenylene diamines of formula (I):

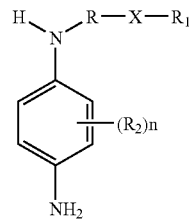

wherein:

X is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4;

said process comprising reducing a nitro compound of formula (II):

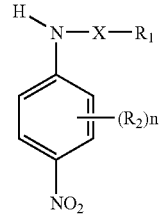

wherein:

x is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4.

9. A cosmetic composition for dyeing fibers, comprising, in a medium that is suitable for dyeing, at least one compound chosen from those of formula (I) and the addition salts thereof:

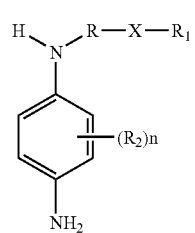

wherein:
X is chosen from SO$_2$ and sulfur;
if X is SO$_2$, R is chosen from linear and branched, saturated and unsaturated C$_2$-C$_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
if X is sulfur, R is chosen from branched, saturated, and unsaturated C$_1$-C$_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
R$_1$ is chosen from amino radicals, aryl radicals, and linear and branched, saturated and unsaturated C$_1$-C$_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;
R$_2$ is chosen from hydrogen, halogen atoms, and radicals chosen from alkyl, alkoxy, alkoxyalkyl, hydroxyalkoxy, monohydroxyalkyl, and polyhydroxyalkyl; and
n is an integer ranging from 1 to 4;
with the proviso that the compound of formula (I) is not:
2-(4-Amino-3-methylphenylamino)ethanesulfonamide,
2-(4-Aminophenylamino)ethanesulfonic acid diethylamide,
N-[2-(4-Amino-2-methylphenylamino)ethyl]methanesulfonamide, or
N-[2-(4-Aminophenylamino)ethyl]methanesulfonamide.

10. The cosmetic composition according to claim 9, wherein R is chosen from linear and branched C$_2$-C$_5$ alkylene radical, which may be substituted with a radical chosen from —OH, —COOCH$_3$, and —COOCH$_2$CH$_3$, wherein at least one carbon atom of the alkylene radical is optionally replaced with at least one heteroatom chosen from oxygen, nitrogen, and sulfur.

11. The cosmetic composition according to claim 9, wherein R$_1$ is chosen from alkyl, aryl, arylalkyl, and hydroxyalkyl groups, and secondary and tertiary amine groups.

12. The cosmetic composition according to claim 9, wherein R$_2$ is a methyl.

13. The composition according to claim 9, wherein the compound of formula (I) is chosen from:
N-[2-(4-aminophenylamino)ethyl]benzenesulfonamide,
2-(4-Aminophenylamino)ethanesulfonic acid (tetrahydrofuran-2-ylmethyl)amide,
2-(4-Aminophenylamino)ethanesulfonic acid methylamide,
2-(4-Aminophenylamino)ethanesulfonic acid (2-hydroxyethyl)amide,
N-[2-(4-Aminophenylamino)ethyl]methanesulfonamide,
2-(4-Aminophenylamino)ethanesulfonic acid diethylamide,
2-(4-Aminophenylamino)ethanesulfonic acid amide,
N-[2-(4-Aminophenylamino)ethyl]-N-methylmethanesulfonamide,
N-[4-(4-Aminophenylamino)butyl]methanesulfonamide,
2-(4-Aminophenylamino)ethanesulfonic acid bis(2-hydroxyethyl)amide,
N-(2-Methanesulfonyl-ethyl)benzene-1,4-diamine,
Methanethiosulfonic acid S-[2-(4-aminophenyiamino)ethyl]ester,
Sulfuric acid mono[2-(4-aminophenylamino)ethyl]ester,
Thiosulfuric acid S-[2-(4-aminophenylamino)ethyl]ester,
2-(4-Aminophenylamino)-4-methylsulfanylbutyric acid methyl ester,
2-(4-Aminophenylamino)-3-benzylsulfanylpropan-1-ol,
2-(4-Aminophenylamino)-3-benzylsulfanylpropionic acid ethyl ester,
2-(4-Aminophenylamino)-3-benzylsulfanylpropionic acid methyl ester,
2-(4-Aminophenylamino)-4-methylsulfanylbutyric acid ethyl ester,
N-[2-(4-Amino-2-methylphenylamino)ethyl]benzenesulfonamide,
2-(4-Amino-2-methylphenylamino)ethanesulfonic acid (tetrahydrofuran-2-ylmethyl)amide,
2-(4-Amino-2-methylphenylamino)ethanesulfonic acid methylamide,
2-(4-Amino-2-methylphenylamino)ethanesulfonic acid (2-hydroxyethyl)amide,
N-[2-(4-Amino-2-methylphenylamino)ethyl]methanesulfonamide,
2-(4-Amino-2-methylphenylamino)ethanesulfonic acid diethylamide,
2-(4-Amino-2-methylphenylamino)ethanesulfonic acid amide,
N-[2-(4-Amino-2-methylphenylamino)ethyl]-N-methylmethanesulfonamide,
N-[4-(4-Amino-2-methylphenylamino)butyl]methanesulfonamide,
2-(4-Amino-2-methylphenylamino)ethanesulfonic acid bis(2-hydroxyethyl)amide,
N-1-(2-Methanesulfonyl-ethyl)-2-methylbenzene-1,4-diamine,
Methanethiosulfonic acid S-[2-(4-amino-2-methylphenylamino)ethyl]ester,
Sulfuric acid mono[2-(4-amino-2-methylphenylamino)ethyl]ester,
Thiosulfuric acid S-[2-(4-amino-2-methyl phenylamino)ethyl]ester,
2-(4-Amino-2-methylphenylamino)-4-methylsulfanylbutyric acid methyl ester,
2-(4-Amino-2-methylphenylamino)-3-benzylsulfanyl propan-1-ol,
2-(4-Amino-2-methylphenylamino)-3-benzylsulfanyl propionic acid ethyl ester,
2-(4-Amino-2-methylphenylamino)-3-benzylsulfanyl propionic acid methyl ester,
2-(4-Amino-2-methylphenylamino)-4-methylsulfanylbutyric acid ethyl ester,
N-[2-(4-Amino-3-methylphenylamino)ethyl]benzenesulfonamide,
2-(4-Amino-3-methylphenylamino)ethanesulfonic acid (tetrahydrofuran-2-ylmethyl)amide, 2-(4-Amino-3-methylphenylamino)ethanesulfonic acid methylamide,
2-(4-Amino-3-methylphenylamino)ethanesulfonic acid (2-hydroxyethyl)amide,
2-(4-Amino-3-methylphenylamino)ethanesulfonic acid diethylamide,
2-(4-Amino-3-methylphenylamino)ethanesulfonic acid amide,
N-[2-(4-Amino-3-methylphenylamino)ethyl]-N-methyl-methanesulfonamide,
N-[4-(4-Amino-3-methylphenylamino)butyl]methanesulfonamide
2-(4-Amino-3-methylphenylamino)ethanesulfonic acid bis(2-hydroxyethyl)amide,
N-4-(2-Methanesulfonyl-ethyl )-2-methyl benzene-1,4-diamine,
Methanethiosulfonic acid S-[2-(4-amino-3-methylphenylamino)ethyl]ester,
Sulfuric acid mono[2-(4-amino-3-methylphenylamino)ethyl]ester,
Thiosulfuric acid S-[2-(4-amino-3-methylphenylamino)ethyl]ester,
2-(4-Amino-3-methylphenylamino)-4-methylsulfanyl butyric acid methyl ester,
2-(4-Amino-3-methylphenylamino)-3-benzylsulfanylpropan-1-ol,
2-(4-Amino-3-methylphenylamino)-3-benzylsulfanylpropionic acid ethyl ester,
2-(4-Amino-3-methylphenylamino)-3-benzylsulfanylpropionic acid methyl ester,
2-(4-Amino-3-methylphenylamino)-4-methylsulfanyl butyric acid ethyl ester,
N-[2-(4-Amino-3-methylphenylamino)ethyl]methanesulfonamide, and the addition salts thereof.

14. The cosmetic composition according to claim 9, wherein the addition salts of the compounds of formula (I) are acid addition salts and are chosen from hydrochlorides, hydrobromides, sulfates, citrates, succinates, tartrates, lactates, tosylates, benzenesulfonates, phosphates, and acetates.

15. The cosmetic composition according to claim 9, wherein the at least one compound of formula (I) is present in an amount ranging from 0.0001% to 20% by weight, relative to the total weight of the composition.

16. The cosmetic composition according to claim 15, wherein the at least one compound of formula (I) is present in an amount ranging from 0.005% to 6% by weight, relative to the total weight of the composition.

17. The cosmetic composition according to claim 9, wherein the medium that is suitable for dyeing consists of water or comprises a mixture of water and at least one organic solvent chosen from branched and unbranched $C_1$-$C_4$ lower alcohols; polyols and polyol ethers; and aromatic alcohols.

18. The cosmetic composition according to claim 9, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins, and provitamins.

19. The cosmetic composition according to claim 18, wherein the at least one cosmetic adjuvant is present in an amount, for each adjuvant, ranging from 0.01% to 20% by weight, relative to the total weight of the composition.

20. The cosmetic composition according to claim 9, further comprising at least one oxidation coupler chosen from meta-phenylenediamines, meta-aminophenols, meta-diphenols, naphthalene-based couplers, heterocyclic couplers, and the addition salts thereof.

21. The cosmetic composition according to claim 20, wherein the at least one oxidation coupler is present in an amount ranging from 0.0001% to 20% by weight, relative to the total weight of the composition.

22. The cosmetic composition according to claim 9, further comprising at least one additional oxidation base other those of formula (I), chosen from para-phenylenediamines, bis(phenyl)alkylenediamines, para-aminophenols, ortho-aminophenols, heterocyclic bases, and the addition salts thereof.

23. The cosmetic composition according to claim 22, wherein the at least one additional oxidation base is present in an amount ranging from 0.0001% to 20% by weight, relative to the total weight of the composition.

24. The cosmetic composition according to claim 9, further comprising at least one direct dye chosen from cationic and natural direct dyes.

25. A process for dyeing keratin fibers, comprising applying to the fibers a composition comprising, in a medium that is suitable for dyeing, at least one compound chosen from compounds of formula (I) and the addition salts thereof, and leaving the cosmetic composition on the keratin fibers, in the presence of an oxidizing agent, for a time that is sufficient to develop a desired coloration:

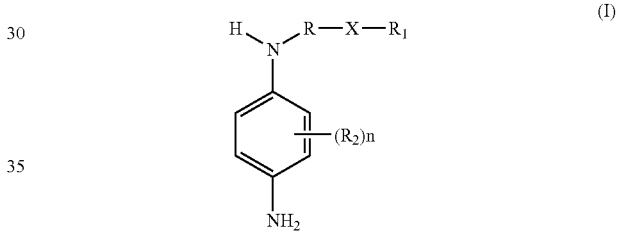

wherein:
x is chosen from $SO_2$ and sulfur;
if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;
$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4;

with the proviso that the compound of formula (I) is not:

2-(4-Amino-3-methylphenylamino)ethanesulfonamide, 2-(4-Aminophenylamino)ethanesulfonic acid diethylamide, N-[2-(4-Amino-2-methylphenylamino)ethyl]methanesulfonamide, or N-[2-(4-Aminophenylamino)ethyl]methanesulfonamide.

26. A ready-to-use cosmetic composition, comprising, in a medium that is suitable for dyeing, at least one compound chosen from those of formula (I) and the addition salts thereof:

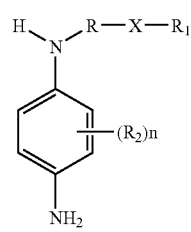

(I)

wherein:

X is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4;

with the proviso that the compound of formula (I) is not:

2-(4-Amino-3-methylphenylamino)ethanesulfonamide, 2-(4-Aminophenylamino)ethanesulfonic acid diethylamide, N-[2-(4-Amino-2-methylphenylamino)ethyl]methanesulfonamide, or N-[2-(4-Aminophenylamino)ethyl]methanesulfonamide, and at least one oxidizing agent chosen from hydrogen peroxide, urea peroxide, alkali metal bromates, persalts, peracids, and oxidase enzymes.

27. A ready to use composition according to claim 26, wherein said at least one oxdizing agent is hydrogen peroxide.

28. A multi-compartment kit, comprising at least one first compartment comprising at least one cosmetic composition for dyeing keratin fibers, comprising, in a medium that is suitable for dyeing, at least one compound chosen from those of formula (I) and the addition salts thereof:

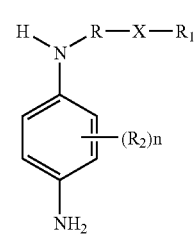

(I)

wherein:

x is chosen from $SO_2$ and sulfur;

if X is $SO_2$, R is chosen from linear and branched, saturated and unsaturated $C_2$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

if X is sulfur, R is chosen from branched, saturated, and unsaturated $C_1$-$C_{10}$ alkylene radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, wherein at least one carbon atom of the alkylene radical is optionally replaced with at least one entity chosen from carbonyl functional groups and heteroatoms chosen from oxygen, nitrogen, and sulfur;

$R_1$ is chosen from amino radicals, aryl radicals, and linear and branched, saturated and unsaturated $C_1$-$C_{10}$ alkyl radicals, which are unsubstituted or substituted with a halogen atom or with at least one group chosen from hydroxyl, alkoxy, amino, monoalkylamino, dialkylamino, alkylcarbonyl, carboxyl, amido, alkoxycarbonyl, monoalkylaminocarbonyl, and dialkylaminocarbonyl groups, and saturated and unsaturated 5- or 6-atom heterocycles, wherein at least one carbon atom of the alkyl radical is optionally replaced with at least one entity chosen from carbonyl functional groups and heteroatoms chosen from oxygen, nitrogen, and sulfur;

$R_2$ is chosen from hydrogen, halogen atoms, and radicals chosen from alkyl, alkoxy, alkoxyalkyl, hydroxyalkoxy, monohydroxyalkyl, and polyhydroxyalkyl; and n is an integer ranging from 1 to 4;

with the proviso that the compound of formula (I) is not:

2-(4-Amino-3-methylphenylamino)ethanesulfonamide, 2-(4-Aminophenylamino)ethanesulfonic acid diethylamide, N-[2-(4-Amino-2-methylphenylamino)ethyl]methanesulfonamide, or N-[2-(4-Aminophenylamino)ethyl]methanesulfonamide, and at least one second compartment comprising at least one oxidizing agent.

29. The process according to claim 25, wherein said keratin fibers are human hair.

* * * * *

UNITED STATES PATENT AND TRADEMARK OFFICE
CERTIFICATE OF CORRECTION

PATENT NO.        : 7,347,879 B2
APPLICATION NO.   : 11/066457
DATED             : March 25, 2008
INVENTOR(S)       : Sabelle et al.

It is certified that error appears in the above-identified patent and that said Letters Patent is hereby corrected as shown below:

On the Title Page, and col. 1, line 2, Item (54) on the title page, "PARA-PHENYLENEDIAMINES DYE" should read -- PARA-PHENYLENEDIAMINES, DYE --.

On the Title Page, Item (73), "L'Oreál, S.A.," should read -- L'Oréal S.A., --.

Claim 5, column 84, line 61, "2-(4-Aminophenylamino)-4-methylsulfanyl butyric" should read -- 2-(4-Aminophenylamino)-4-methylsulfanylbutyric --.

Claim 5, column 85, line 1, "2-(4-Aminophenylamino)-4-methylsulfanyl butyric" should read -- 2-(4-Aminophenylamino)-4-methylsulfanylbutyric --.

Claim 5, column 85, lines 3-4, "N-[2-(4-Amino-2-methyl phenylamino)ethyl]benzenesulfonamide," should read -- N-[2-(4-Amino-2-methylphenylamino)ethyl]benzenesulfonamide, --.

Claim 5, column 85, lines 30-31, "2-(4-Amino-2-methylphenylamino)-3-benzylsulfanylpropionic" should read -- 2-(4-Amino-2-methylphenylamino)-3-benzylsulfanylpropionic --.

Claim 5, column 85, line 36, "2-(4-Amino-3-methyl phenylamino)ethanesulfonic" should read -- 2-(4-Amino-3-methylphenylamino)ethanesulfonic --.

Claim 5, column 85, lines 42-43, "2-(4-Amino-3-methylphenylamino)-4-methylsulfanyl butyric" should read -- 2-(4-Amino-3-methylphenylamino)-4-methylsulfanylbutyric --.

Claim 5, column 85, lines 63-64, "2-(4-Amino-3-methylphenylamino)-3-benzylsulfanylpropionic" should read -- 2-(4-Amino-3-methylphenylamino)-3-benzylsulfanylpropionic --.

Claim 5, column 85, lines 65-66, "2-(4-Amino-3-methylphenylamino)-3-benzylsulfanyl propionic" should read -- 2-(4-Amino-3-methylphenylamino)-3-benzylsulfanylpropionic --.

UNITED STATES PATENT AND TRADEMARK OFFICE
CERTIFICATE OF CORRECTION

PATENT NO. : 7,347,879 B2
APPLICATION NO. : 11/066457
DATED : March 25, 2008
INVENTOR(S) : Sabelle et al.

It is certified that error appears in the above-identified patent and that said Letters Patent is hereby corrected as shown below:

Claim 7, column 86, lines 12-20,

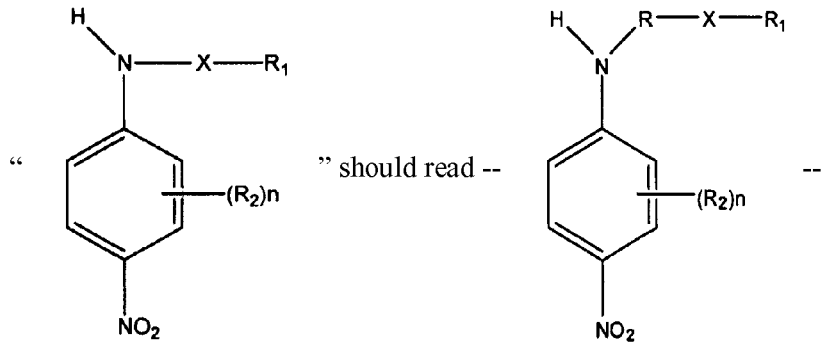

Claim 7, column 86, line 24, "x is" should read -- X is --.

Claim 8, column 88, lines 3-11,

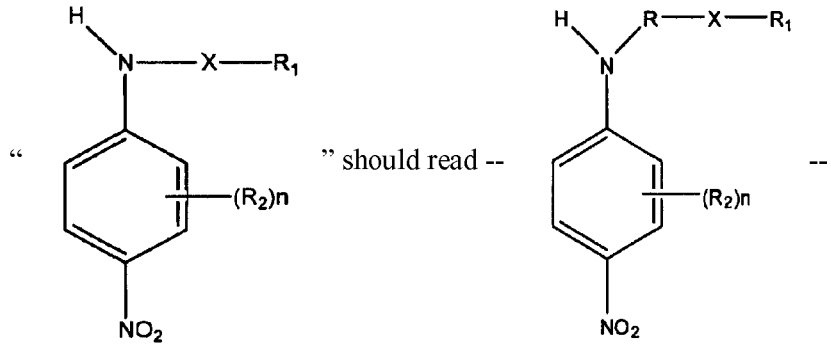

Claim 8, column 88, line 14, "x is" should read -- X is --.

Claim 13, column 90, lines 13-14, "S-[2-(4-aminophenyiamino) ethyl]ester," should read -- S-[2-(4-aminophenylamino)ethyl] ester, --.

UNITED STATES PATENT AND TRADEMARK OFFICE
CERTIFICATE OF CORRECTION

PATENT NO.       : 7,347,879 B2
APPLICATION NO.  : 11/066457
DATED            : March 25, 2008
INVENTOR(S)      : Sabelle et al.

It is certified that error appears in the above-identified patent and that said Letters Patent is hereby corrected as shown below:

Claim 13, column 90, lines 52-53, "S-[2-(4-amino-2-methyl phenylamino)ethyl]ester," should read -- S-[2-(4-amino-2-methylphenylamino)ethyl] ester, --.

Claim 13, column 90, lines 56-57, "2-(4-Amino-2-methylphenylamino)-3-benzylsulfanyl propan-1-ol," should read -- 2-(4-Amino-2-methylphenylamino)-3-benzylsulfanylpropan-1-ol, --.

Claim 13, column 90, lines 58-59, "2-(4-Amino-2-methylphenylamino)-3-benzylsulfanyl propionic" should read -- 2-(4-Amino-2-methylphenylamino)-3-benzylsulfanylpropionic --.

Claim 13, column 90, lines 60-61, "2-(4-Amino-2-methylphenylamino)-3-benzylsulfanyl propionic" should read -- 2-(4-Amino-2-methylphenylamino)-3-benzylsulfanylpropionic --.

Claim 13, column 91, line 5, "2-(4-Amino-3-methylphenylamino)ethanesulfonic" should read -- 2-(4-Amino-3-methylphenylamino)ethanesulfonic --.

Claim 13, column 91, lines 15-16, "N-4-(2-Methanesulfonyl-ethyl)-2-methyl benzene-1,4-diamine," should read -- N-4-(2-Methanesulfonyl-ethyl)-2-methylbenzene-1,4-diamine, --.

Claim 13, column 91, line 17, "Methanethiosulfonic" should read -- Methanethiosulfonic --.

Claim 13, column 91, lines 23-24, "2-(4-Amino-3-methylphenylamino)-4-methylsulfanyl butyric" should read -- 2-(4-Amino-3-methylphenylamino)-4-methylsulfanylbutyric --.

Claim 13, column 91, lines 31-32, "2-(4-Amino-3-methylphenylamino)-4-methylsulfanyl butyric" should read -- 2-(4-Amino-3-methylphenylamino)-4-methylsulfanylbutyric --.

Claim 22, column 92, line 9, "other those" should read -- other than those --.

UNITED STATES PATENT AND TRADEMARK OFFICE
CERTIFICATE OF CORRECTION

PATENT NO. : 7,347,879 B2
APPLICATION NO. : 11/066457
DATED : March 25, 2008
INVENTOR(S) : Sabelle et al.

It is certified that error appears in the above-identified patent and that said Letters Patent is hereby corrected as shown below:

Claim 25, column 92, line 41, "x is" should read -- X is --.

Claim 28, column 94, line 46, "x is" should read -- X is --.

Signed and Sealed this

Twenty-second Day of July, 2008

JON W. DUDAS
*Director of the United States Patent and Trademark Office*